(12) United States Patent
Vilicich et al.

(10) Patent No.: US 12,115,203 B1
(45) Date of Patent: Oct. 15, 2024

(54) CHEMICAL PROCESSES AND APPARATUSES FOR EXTRACTING ORGANIC COMPOUNDS FROM BIOMASS WITH VOLATILE ORGANIC COMPOUND REMOVAL

(71) Applicant: Advanced Engineering Concepts, Inc., San Pedro, CA (US)

(72) Inventors: Andrew J. Vilicich, San Pedro, CA (US); Ludwig C. Zelt, San Pedro, CA (US)

(73) Assignee: Advanced Engineering Concepts, Inc., San Pedro, CA (US)

( * ) Notice: Subject to any disclaimer, the term of this patent is extended or adjusted under 35 U.S.C. 154(b) by 0 days.

(21) Appl. No.: 18/665,693

(22) Filed: May 16, 2024

Related U.S. Application Data

(60) Provisional application No. 63/573,351, filed on Apr. 2, 2024, provisional application No. 63/515,526, filed on Jul. 25, 2023.

(51) Int. Cl.
| | | |
|---|---|---|
| *A61K 36/185* | (2006.01) | |
| *A61K 36/81* | (2006.01) | |
| *B01D 3/02* | (2006.01) | |
| *B01D 3/10* | (2006.01) | |
| *B01D 3/14* | (2006.01) | |
| *B01D 5/00* | (2006.01) | |
| *B01D 9/00* | (2006.01) | |
| *B01D 11/02* | (2006.01) | |

(52) U.S. Cl.
CPC .......... *A61K 36/3482* (2024.05); *A61K 36/81* (2013.01); *B01D 3/02* (2013.01); *B01D 3/10* (2013.01); *B01D 3/143* (2013.01); *B01D 5/006* (2013.01); *B01D 9/0004* (2013.01); *B01D 11/0288* (2013.01); *B01D 11/0296* (2013.01); *A61K 2236/35* (2013.01); *A61K 2236/37* (2013.01); *A61K 2236/55* (2013.01)

(58) Field of Classification Search
None
See application file for complete search history.

(56) References Cited

U.S. PATENT DOCUMENTS 5,449,010 A    12/1995   Taricco

*Primary Examiner* — Michael V Meller
(74) *Attorney, Agent, or Firm* — Akerman LLP

(57) ABSTRACT

Disclosed embodiments include systems and methods for obtaining desired organic compounds from harvested biomass. Some examples include an extraction vessel and a distillery system, where the extraction vessel is configured to wash harvested biomass with a process solvent to obtain a liquid extract, and where the distillery system is configured to distill the extract to separate the process solvent from the extract and obtain a distillate from the extract. Some embodiments additionally include a speedloader configured to load harvested biomass into the extraction vessel and a discharge gantry configured to remove processed biomass from the extraction vessel. In some embodiments, the extraction vessel, distillery system, speedloader, and discharge gantry are mobile and can be deployed "in field" at a harvest location.

12 Claims, 11 Drawing Sheets

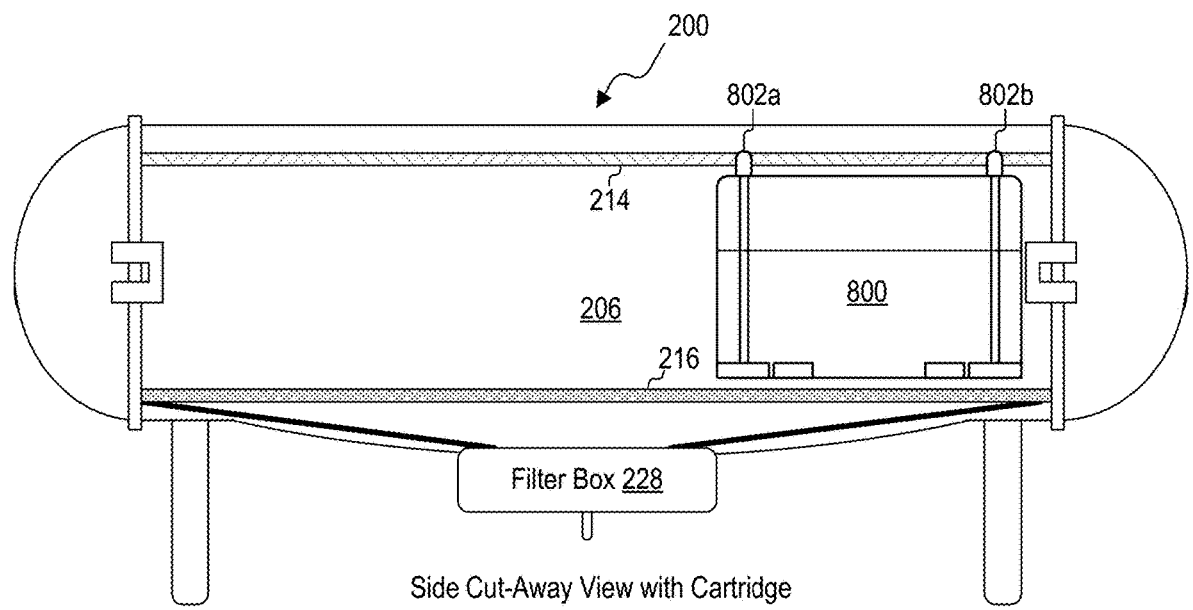
Side Cut-Away View with Cartridge
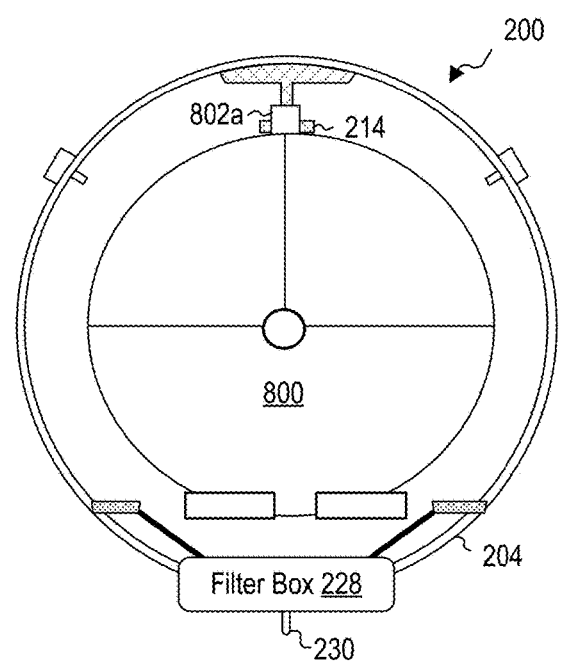
End Cut-Away View with Cartridge
FIG. 2C

CHEMICAL PROCESSES AND APPARATUSES FOR EXTRACTING ORGANIC COMPOUNDS FROM BIOMASS WITH VOLATILE ORGANIC COMPOUND REMOVAL

CROSS REFERENCE TO RELATED APPLICATIONS

This application claims priority to (i) U.S. Provisional App. 63/515,526 titled "Chemical Processes and Apparatuses for Extracting Organic Compounds from Biomass," filed on Jul. 25, 2023, and (ii) U.S. Provisional App. 63/573,351 titled "Chemical Processes And Apparatuses For Extracting Organic Compounds From Biomass With Volatile Organic Compound Removal," filed on Apr. 2, 2024. The entire contents of U.S. Provisional Apps. 63/515,526 and 63/573,351 are incorporated herein by reference.

SUMMARY

Disclosed embodiments relate generally to systems and methods for extracting desired organic compounds from organic biomass. In some embodiments, the organic compounds include oils. The disclosed embodiments are suitable for use with any organic biomass containing organic oils, including but not limited to, *cannabis*, tobacco, palm seeds, olives, almonds, walnuts, or other biomass comprising organic oils.

In some embodiments, the system components are mobile and can be deployed "infield" at the point of harvest, thereby enabling extraction of the desired organic compounds from harvested biomass "infield" without requiring transport of the harvested biomass to an offsite location for processing.

The infield processing capability enabled by the disclosed systems and methods is advantageous because infield processing results in less handling and transportation of the harvested plants as compared to traditional approaches that require transporting harvested plants to a remote processing center. Particularly for *cannabis* plants, excess handling and transportation tends to cause trichomes containing the desired organic compounds to break off of the *cannabis* plant. Since a *cannabis* plant with more intact trichomes can produce more organic compound than a *cannabis* plant with fewer intact trichomes, the infield processing embodiments disclosed herein can generate more organic compounds from the same amount of harvested *cannabis* plants as compared to traditional approaches that require packaging and transporting harvested plants to remote locations for processing.

Mobile configurations are sometimes referred to herein as a Mobile Extraction System. Although some components of the disclosed systems are described as being capable of infield deployment, the system components could be deployed in a fixed location, i.e., mobile deployment is an optional feature but not a requirement of such embodiments.

In some embodiments, a mechanical harvester harvests the biomass (i.e., plants) from a field where the biomass is grown. The harvested biomass is then tagged and baled or otherwise packaged for further processing. Some embodiments include packaging the harvested biomass (whole or bucked biomass) into a cartridge for processing.

One or more cartridges (or other suitable packaging) of harvested biomass are loaded into an extraction vessel via a speedloader positioned at an ingress to the extraction vessel. In some embodiments, one or more cartridges of harvested biomass are placed into the speedloader. The speedloader facilitates routing of the cartridges containing the harvested biomass from the speedloader into the extraction vessel.

Once the biomass is loaded into the extraction vessel, the extraction vessel is sealed and a vacuum is drawn within the extraction vessel. While the extraction vessel is under vacuum, a process solvent is applied to the biomass to extract one or more desired organic compounds from the biomass, thereby resulting in (i) an "extract" for further processing and (ii) processed biomass. The extract at this stage includes the desired organic compounds and process solvent, and the processed biomass at this stage includes some residual process solvent.

After applying the process solvent, the vacuum is released and the extraction vessel is returned to atmospheric pressure, thereby causing liquid extract to collect in the bottom of the extraction vessel. The extraction vessel includes an outlet at the bottom via which the extract can be removed from the extraction vessel. In some embodiments, a pipe, tube, hose, or similarly suitable structure is attached to the outlet, and the liquid extract is routed (e.g., via a pump) from the bottom of the extraction vessel to a distillery system.

Some embodiments additionally include a step where the extract is winterized to remove undesirable solids, e.g., fats, lipids, waxes, or other solids before the extract is routed to the distillery system. Winterization in this context includes cooling the liquid extract to precipitate the undesirable solids from the liquid extract, and then filtering the undesirable solids from the liquid extract, resulting in a product sometimes referred to herein as "filtered extract." In some embodiments, the filtration step is performed by a filter box at the bottom of the extraction vessel. This filtered extract is then routed (e.g., via a pump) from the extraction vessel to a distillery system via a pipe, hose, or similarly suitable structure. Some embodiments may not include winterization, and may instead route the liquid extract (i.e., unwinterized, or sometimes referred to as "unfiltered extract") from the extraction vessel to the distillery system.

The distillery system is configured to distill the liquid extract (comprising the desired organic compound and process solvent) received from the extraction vessel. In operation, the distillation performed by the distillery system separates the desired organic compound(s) in the liquid extract (filtered extract or unfiltered extract) from the process solvent, thereby resulting in (i) a distillate comprising the desired organic compound(s) and (ii) process solvent recovered from the extract, sometimes referred to herein as "recovered process solvent."

The distillate produced by the distillery system tends to be thick and viscous. Distillate produced from unfiltered extract tends to be thicker and more viscous than distillate produced from filtered extract because of the undesirable solids within the unfiltered extract. Therefore, some embodiments additionally include adding a transport solvent to the distillate, thereby resulting in a reduced-viscosity distillate. This reduced-viscosity distillate is then routed (e.g., via a pump) from the distillery system to a distillate holding tank. This reduced-viscosity distillate can be further processed to remove the transport solvent and to generate further products from the organic compounds contained in the distillate.

In some embodiments, the recovered process solvent is routed (e.g., via a pump) from the distillery system to a recovered process solvent holding tank. This recovered process solvent can be used in the extraction vessel again when processing another batch of harvested biomass.

Recall that after the extraction vessel has obtained the extract from the biomass, the processed biomass contains some residual process solvent. Some embodiments additionally include recovering at least some of the residual process solvent contained within the processed biomass. Like the recovered process solvent obtained from the distillery system, the residual process solvent recovered from the processed biomass can also be used in the extraction vessel again when processing another batch of harvested biomass.

In some embodiments, recovering the residual process solvent contained within the processed biomass includes lowering the air pressure within the extraction vessel containing the processed biomass and/or applying light to the processed biomass within the extraction vessel, thereby causing at least some of the residual process solvent to evaporate from the processed biomass. This evaporated process solvent is then routed into a process solvent reclamation condenser that is configured to condense the evaporated process solvent into liquid form. This liquid process solvent recovered from the processed biomass can then be routed (e.g., via a pump) to the recovered process solvent holding tank.

After evaporating at least some of the residual process solvent from the processed biomass within the extraction vessel, the processed biomass can be removed from the extraction vessel. In some embodiments, the processed biomass is removed from the extraction vessel via a discharge gantry positioned at an egress to the extraction vessel. In some instances, the discharge gantry at the egress to the extraction vessel contains the same components as the speedloader positioned at the ingress to the extraction vessel. But while the speedloader feeds one or more cartridges containing harvested biomass to the extraction vessel, the discharge gantry receives one or more cartridges containing processed biomass from the extraction vessel.

In some embodiments, a monorail system (and in some instances, a motorized monorail system) configured to extend through the speedloader, extraction vessel, and discharge gantry facilitates the (i) movement of a cartridge containing harvested biomass from the speedloader and into the extraction vessel, (ii) the movement of the cartridge within the extraction vessel before/during/after processing, and (iii) the movement of the cartridge containing the processed biomass from the extraction vessel to the discharge gantry. Alternative embodiments may include a multi-rail (e.g., a side-by-side dual rail) system rather than a monorail system.

Some aspects of the disclosed embodiments for extracting organic compounds from biomass are based in part on the cleaning system disclosed in U.S. Pat. No. 5,449,010, titled "Pressure controlled cleaning system," sometimes referred to herein as the "Near Zero Emissions" machine, or "NZE" Machine. The entire contents of U.S. Pat. No. 5,449,010 are incorporated by reference herein as if set out in full. Specifically, the NZE Machine was developed as a solvent washer and cleaning device, specifically configured to remove grease, oils, flux, and other foreign debris from objects as undesirable. In contrast to the NZE machine, in the embodiments disclosed herein, the washdown materials are not identified as waste products but instead are the sought after compounds. Thus, in contrast to the NZE machine described in U.S. Pat. No. 5,449,010, embodiments disclosed herein are configured to capture and retain the anticipated extracts, remove process solvents from the desired extracts to facilitate further processing of the extracts, recover residual process solvents from processed biomass, and in some instances, reuse process solvents removed from the extract and recovered from the processed biomass.

The disclosed embodiments include a new system comprising one or more (or all) of a speedloader, extraction vessel, distillery system, and discharge gantry that are specially adapted for obtaining desired organic compounds from harvested biomass according to the processes disclosed and described herein. The components of this new system and their constituent sub-systems are new designs that do not rely on prior designs.

For example, some embodiments include vacuum sealing an extraction vessel containing biomass, where the biomass includes a desired organic compound. While the extraction vessel is vacuum sealed, the biomass comprising the desired organic compound within the extraction vessel is washed with a process solvent. In some embodiments, at least some of the process solvent is in vaporized form. In operation, washing the biomass with the process solvent causes at least some of the desired organic compound(s) within the biomass to separate from the biomass and settle in the bottom of the extraction vessel. After the washing process, the extraction vessel contains (i) an extract comprising the desired organic compound and the process solvent and (ii) processed biomass that includes residual process solvent.

Some embodiments further include distilling the extract to separate process solvent within the extract from the desired organic compound within the extract, resulting in (i) recovered process solvent and (ii) a distillate comprising the desired organic compound. In some embodiments, the recovered process solvent is routed to a recovered process solvent holding tank. For the distillate comprising the desired organic compound, some embodiments additionally include creating a reduced-viscosity distillate by adding a transport solvent to the distillate, and then routing the reduced-viscosity distillate to a distillate holding tank.

Certain examples described herein may include none, some, or all of the above described features and/or advantages. Further, additional features and/or advantages may be readily apparent to persons of ordinary skill in the art based on reading the figures, descriptions, and claims included herein.

BRIEF DESCRIPTION OF THE DRAWINGS

For a more complete understanding of the present disclosure and its features and advantages, reference is now made to the following description, taken in conjunction with the accompanying drawings.

FIG. 2C shows the side cut-away view of FIG. 2A and the end cut-away view of FIG. 2B with the extraction vessel containing a cartridge configured to hold biomass according to some embodiments.

DETAILED DESCRIPTION OF THE FIGURES

The example embodiments now will be described more fully hereinafter with reference to the accompanying figures, in which certain example embodiments are shown. The components shown and described with reference to the figures may, however, be embodied in many different forms and should not be construed as limited to the embodiments illustrated herein. Rather, the example embodiments disclosed herein are provided so that this disclosure will be thorough and complete, and will fully convey the scope of the inventions contained herein to those skilled in the art.

When an element is referred to as being "on" another element, it can be directly on the other element or intervening elements may be present there between. As used herein, the term "and/or" includes any and all combinations of one or more of the associated listed items.

Although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section.

As used herein, the singular forms "a," "an," and "the," are intended to include the plural forms as well, unless the context clearly indicates otherwise. It will be further understood that the terms "comprises" and/or "comprising," "includes" and/or "including," and "have" and/or "having," when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," and "upper" or "top," and "inner" or "outer," may be used herein to describe one element's relationship to other elements as illustrated in the figures. It will be understood that relative terms are intended to encompass different orientations of the device in addition to the orientation depicted in the figures.

Unless otherwise defined, all terms used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

I. Overview

Figure 1:
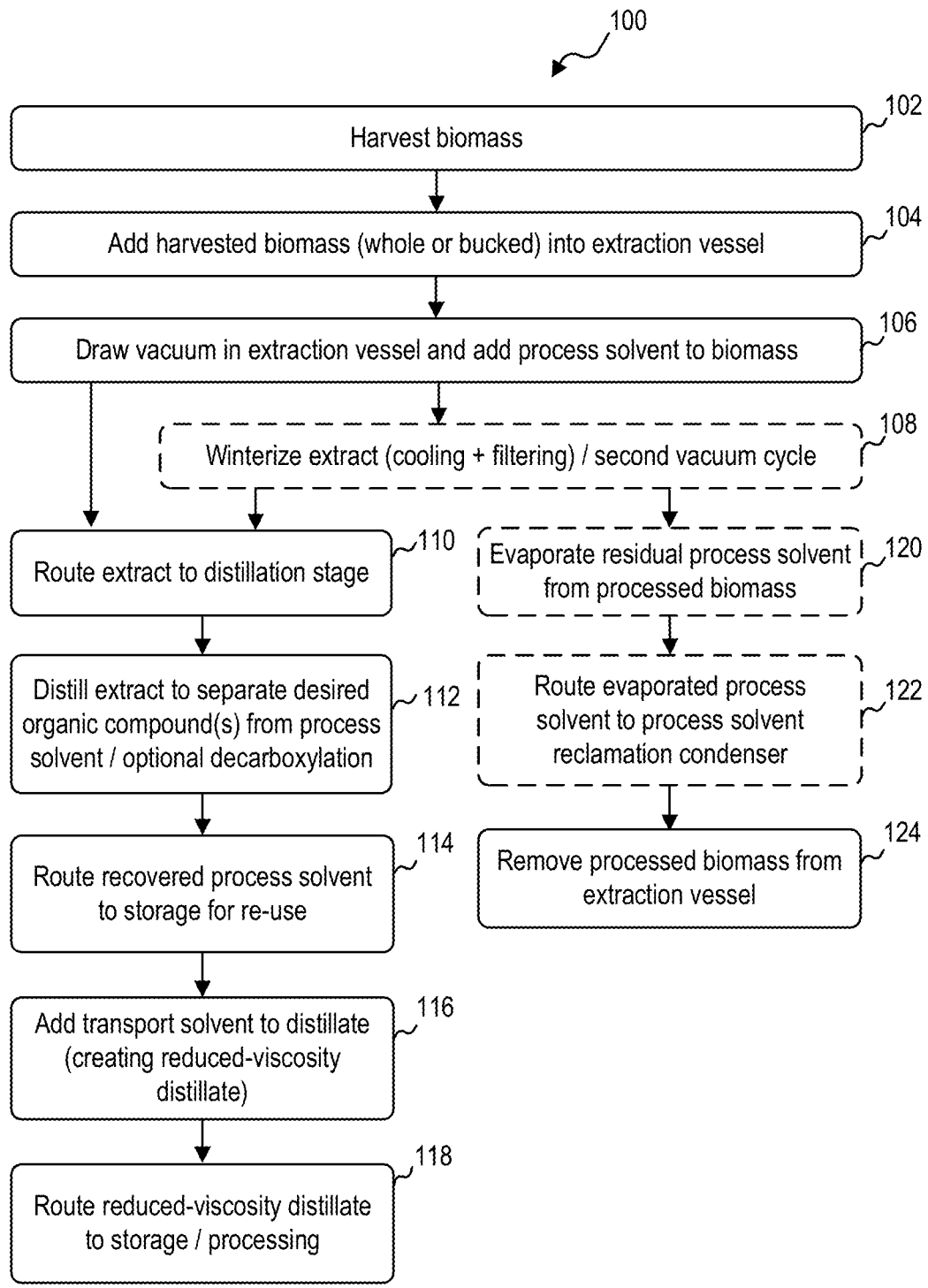
FIG. 1 shows a flow chart depicting aspects of an example process for extracting organic compounds from biomass according to some embodiments.

FIG. 1 shows a flow chart depicting aspects of an example process 100 for extracting organic compounds from biomass according to some embodiments.

Figure 3:
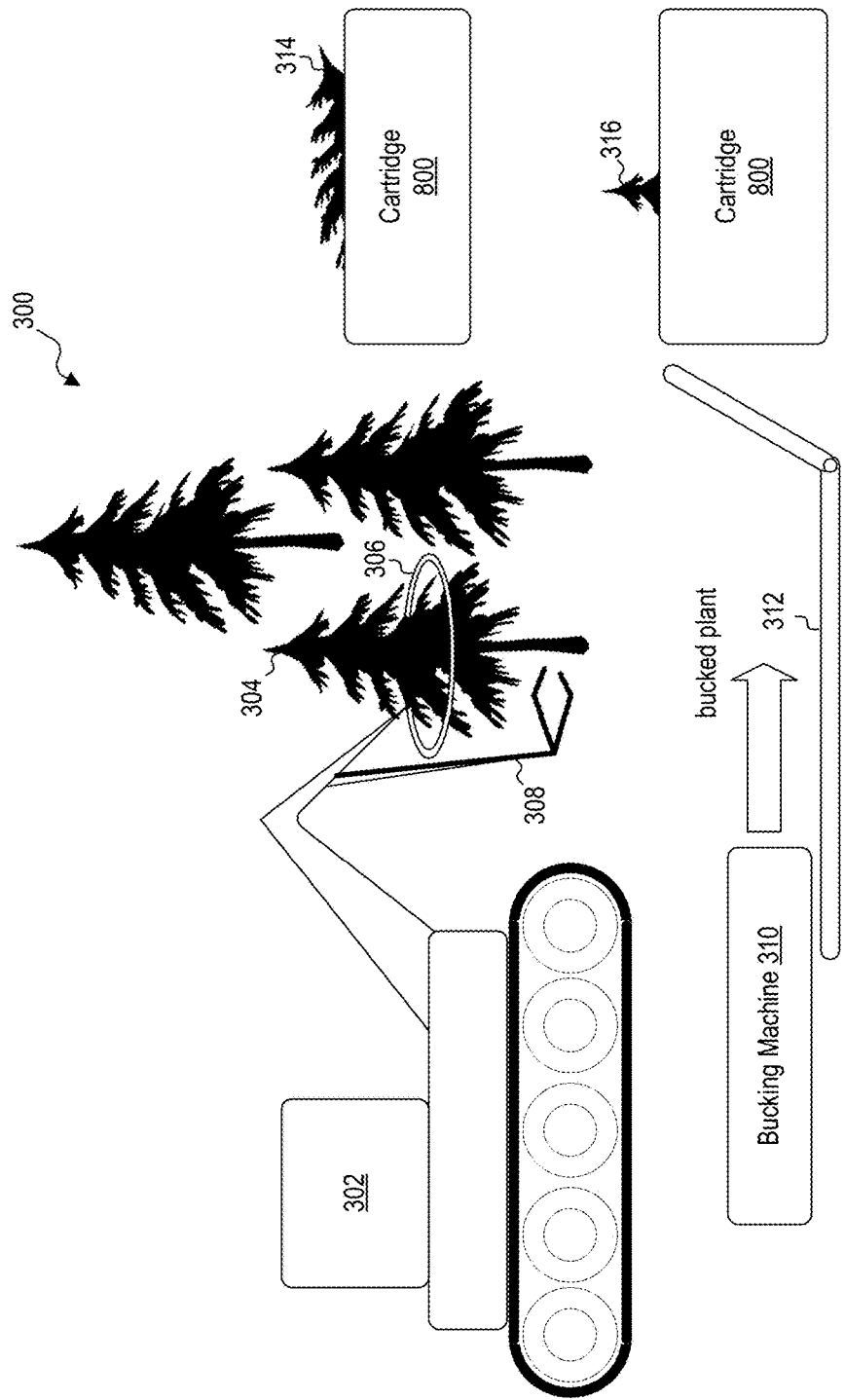
FIG. 3 shows aspects of harvesting and preparing biomass for processing according to some embodiments.

Process 100 begins at block 102, which includes harvesting biomass. In some embodiments, the biomass may be harvested as shown in FIG. 3 or any other suitable harvesting method. In some embodiments, the harvested biomass (whole or bucked) is placed into a cartridge or other suitable packaging to facilitate processing. In some embodiments, the cartridge may be similar to or the same as the cartridge shown in FIGS. 8A and 8B or any other similar mechanism suitable for holding the harvested biomass for processing.

The harvested biomass placed within the cartridge may be wet, dry, or frozen. Similarly, the harvested biomass may be a whole plant or a portion of a plant. In some instances, the harvested biomass is or includes a bucked plant. A bucked plant is a plant that has been cut (i) to retain portions desirable for processing, e.g., leaves, flowers, etc. and (ii) to remove portions that may not be useful for processing, such as roots, stalks, etc.

Figure 8A:
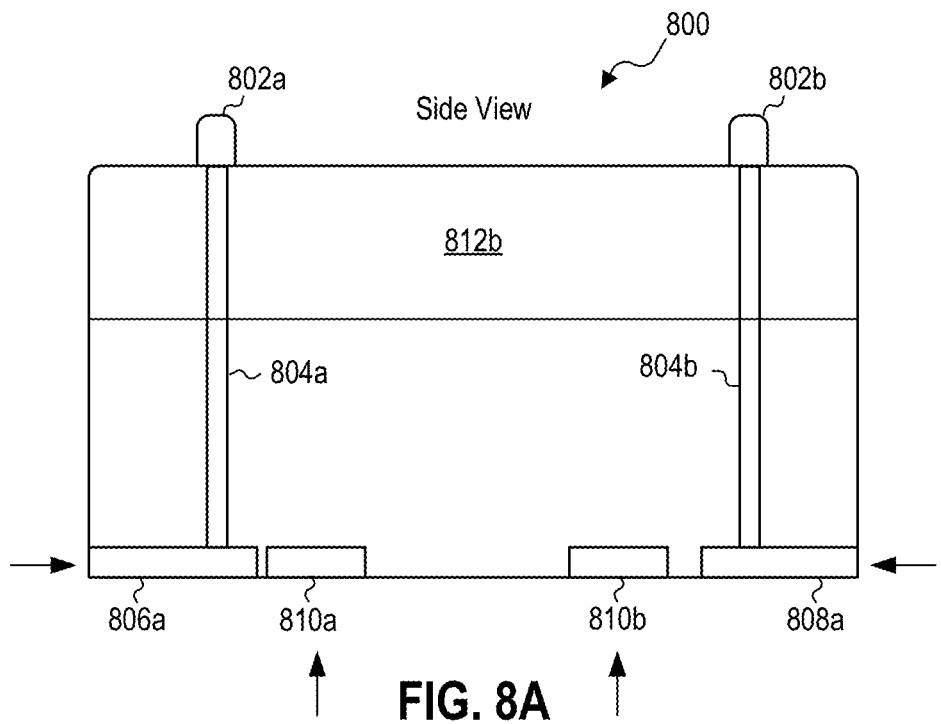
FIG. 8A shows a front view of a material handling cartridge 800 used with a speedloader/discharge gantry and extraction vessel in connection with extracting organic compounds from biomass according to some embodiments.
Figure 8B:
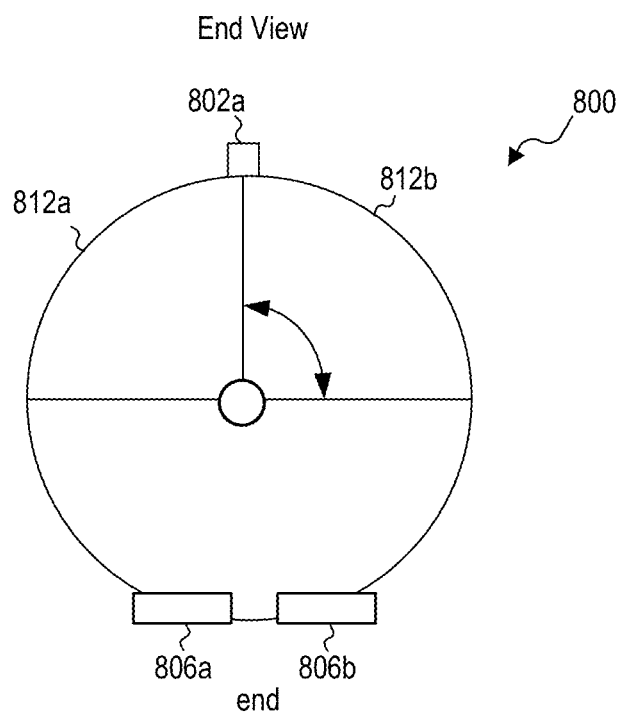
FIG. 8B shows an end view of a material handling cartridge used with a speedloader/discharge gantry and extraction vessel in connection with extracting organic compounds from biomass according to some embodiments.

At block 104, process 100 includes adding the harvested biomass (whole or bucked) into an extraction vessel. In some embodiments, the extraction vessel may be similar to or the same as the extraction vessel shown in FIGS. 2A and 2B or any other suitable extraction vessel configured to perform the extraction vessel functions described herein. Similarly, in some embodiments, the harvested biomass may be added to the extraction vessel via a speedloader. In some embodiments, the speedloader may be the same as the speedloader shown in FIGS. 6A and 6B or any other mechanism that is suitable for loading harvested biomass into the extraction vessel. For example, in some embodiments, the harvested biomass is placed into one or more cartridges as shown in FIGS. 8A and 8B, one or more of the cartridges are placed into a speedloader shown in FIGS. 6A and 6B, and the speedloader routes the one or more cartridges to the extraction vessel shown in FIGS. 2A and 2B for processing.

At block 106, process 100 includes drawing a vacuum in the extraction vessel. While the extraction vessel is under vacuum, block 106 includes applying process solvent to the biomass. In some embodiments, at least some of the process solvent is applied in vapor form. In operation, different process solvents may be used with different biomass. Any of the process solvents disclosed herein can be used.

Block 106 also includes washing the biomass with the process solvent (via one, two, three or more washing cycles), thereby causing organic compounds to separate from the biomass. Next, the extraction vessel is returned to atmospheric pressure (i.e., the vacuum is removed), which causes liquid extract containing the organic compounds to collect in the bottom of the extraction vessel.

Block 108, which is optional, includes winterizing the extract contained within the extraction vessel. In operation, winterization includes cooling the extract to a temperature sufficient to precipitate undesirable solids (e.g., fats, lipids, waxes, or other solids) from the extract, and then filtering the precipitated solids from the extract, thereby resulting in a filtered extract. In some embodiments, the winterization step includes reintroducing the vacuum to the extraction vessel. In some instances, reintroducing the vacuum cools, or at least aids in cooling, the interior of the extraction vessel to achieve a temperature that is sufficiently cold to precipitate the undesirable solids from the liquid extract.

At block 110, the liquid extract (filtered or unfiltered, depending on whether the liquid extract was winterized or not), is routed to a distillery system. In some embodiments, the extraction vessel is connected to the distillery system via one or more pipes, hoses, tubes, or similar structures, and the liquid extract is routed (e.g., via one or more pumps) from the extraction vessel to the distillery system via the pipes, hoses, tubes, or similar structures.

Block 112 includes distilling the liquid extract via the distillery system. The distillery system may be similar to or the same as the distillery system shown in FIG. 7 or any other suitable distillery system configured to perform the distillery system functions described herein.

In operation, the distillery system distills the liquid extract at block 112 to separate the process solvent within the extract from the desired organic compounds within the liquid extract. The distillation process includes heating the liquid extract to a temperature sufficient to boil off the process solvent. Some embodiments may include heating the liquid extract to a temperature sufficient to cause decarboxylation of the liquid extract. The output of the distillation stage at block 112 includes (i) a distilled extract that contains the desired organic compounds and (ii) recovered process solvent. The distilled extract containing the desired organic compounds is sometimes referred to herein as the distillate.

At block 114, the recovered process solvent generated by the distillery system is routed from the distillery system to a recovered process solvent storage tank for reuse. For example, in some embodiments, the distillery system is connected to the recovered process solvent storage tank via one or more pipes, hoses, tubes, or similar structures, and the recovered process solvent is routed (e.g., via one or more pumps) from the distillery system to the recovered process solvent storage tank via the pipes, hoses, tubes, or similar structures.

At block 116, a transport solvent is added to the distillate to reduce the viscosity of the distillate and make it easier to pump from the distillery system to a distillate holding tank. The mixture of the distillate and the transport solvent is sometimes referred to herein as reduced-viscosity distillate.

At block 118, the reduced-viscosity distillate is routed from the distillery system to a distillate storage tank. For example, in some embodiments, the distillery system is connected to the distillate storage tank via one or more pipes, hoses, tubes, or similar structures, and the reduced-viscosity distillate is routed (e.g., via one or more pumps) from the distillery system to the distillate storage tanks via the pipes, hoses, tubes, or similar structures.

After the extract has been routed from the extraction vessel to the distillation system, the extraction vessel still contains processed biomass. This processed biomass contains residual process solvent. In some instances, it may be desirable to remove the residual process solvent from the processed biomass, which is performed at blocks 120 and 122. Blocks 120 and 122 are optional.

At block 120, the residual process solvent is evaporated from the processed biomass by one or both of (i) lowering the air pressure within the extraction vessel and/or (ii) applying light consistent with natural sunlight (including visible light, ultraviolet, and infrared wavelengths) to the processed biomass. In operation, lowering the air pressure within the extraction vessel reduces the air pressure on the surface of the processed biomass, which tends to make it easier for the process solvent to evaporate. Further, as the molecules of the process solvent absorb the light emitted from light source, the molecules tend to experience an increase in heat, which enables them to gain sufficient energy to transition from the liquid phase to the gaseous phase.

Block 122 includes routing (e.g., via a fan or other air source) air containing the evaporated process solvent from the extraction vessel to a process solvent reclamation condenser. In operation, the process solvent reclamation condenser is configured to convert the evaporated process solvent back into a liquid form so that it can be either be used again or disposed of.

Recovering the process solvent entrained in the processed biomass at blocks 120 and 122 helps both (i) reduce the cost of implementing the process by enabling reclamation of the process solvent entrained in the processed biomass for later reuse and (ii) avoid byproduct containing excess process solvents, which can, in some instances, make the processed biomass suitable for a wider range of uses.

Finally, at block 124, the processed biomass is removed from the extraction vessel. In some embodiments, the processed biomass may be removed from the extraction vessel via a discharge gantry. In some embodiments, the discharge gantry may be the same as the discharge gantry shown in FIGS. 6A and 6B or any other mechanism that is suitable for removing processed biomass from the extraction vessel. For example, recall that the harvested biomass was initially loaded into a cartridge that was placed into a speedloader configured to load the cartridge into the extraction vessel. After processing within the extraction vessel, the cartridge containing the processed biomass are routed from the extraction vessel to the discharge gantry.

II. Extraction Vessel

Figure 2A:
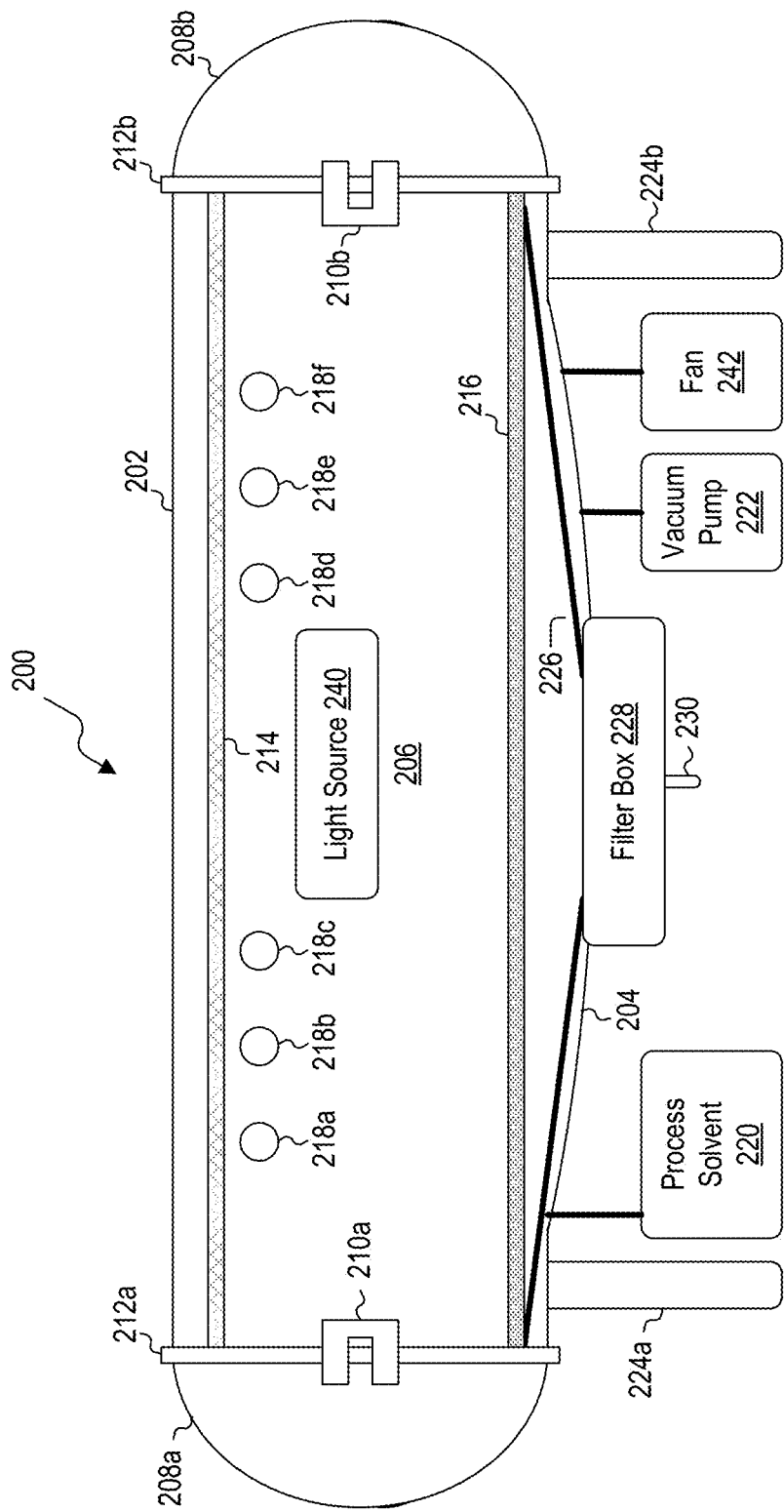
FIG. 2A shows a side cut-away view of an extraction vessel used in connection with extracting organic compounds from biomass according to some embodiments.
Figure 2B:
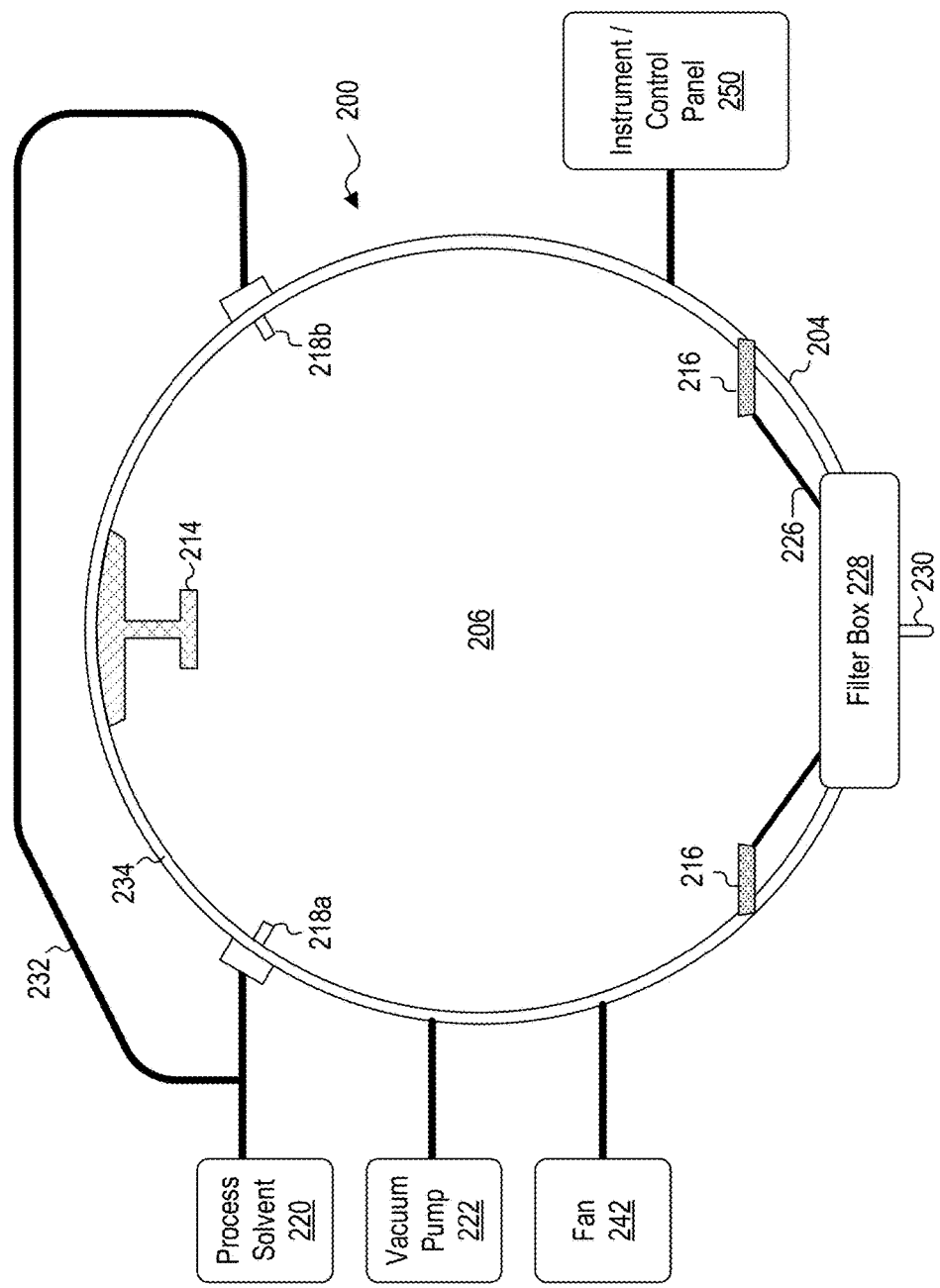
FIG. 2B shows an end cut-away view of an extraction vessel used in connection with extracting organic compounds from biomass according to some embodiments.

FIG. 2A shows a side cut-away view of an extraction vessel 200 used in connection with extracting organic compounds from biomass according to some embodiments. FIG. 2B shows an end cut-away view of an extraction vessel used in connection with extracting organic compounds from biomass according to some embodiments. And FIG. 2C shows the side cut-away view of FIG. 2A and the end cut-away view of FIG. 2B with the extraction vessel containing a cartridge configured to hold biomass according to some embodiments.

The extraction vessel 200 depicted in FIG. 2A has a flat top 202 (or substantially flat top) and a conical (or substantially conical) bottom 204. The extraction vessel 200 is supported at each end by saddles 224a and 224b. The interior space 206 of the extraction vessel 200 is configured to accommodate biomass for processing. In some embodiments, the interior space 206 is configured to accommodate one or more cartridges as shown in FIG. 2C. In operation, the cartridges 800 contain the biomass processed by the system. Additional details on the cartridges 800 shown in FIG. 2C are described with reference to FIGS. 8A and 8B.

The extraction vessel 200 includes at least a first door 208a and a second door 208b. The first door 208a can be opened via a first hinge 210a for the first door 208a. When closed, the first door 208a interfaces with a first locking ring 212a of the extraction vessel 200 to form an airtight seal so that a vacuum can be drawn within the extraction vessel 200. The second door 208b is located at the opposite end of the extraction vessel 200 from the first door 208a. The second door 208b can be opened via a second hinge 210b for the second door 208b. Similar to the first door 208a, when closed, the second door interfaces with a second locking ring 212b of the extraction vessel 200 to form an airtight seal so that a vacuum can be drawn within the extraction vessel 200.

When sealed, the extraction vessel 200 is capable of withstanding a working pressure of up to about 150 pounds per square inch (psi). Withstanding a working pressure of 150 psi can be beneficial when dealing with flammable process solvents to guard against injury or damage caused by potential accidental ignition of the process solvents. In some instances, the extraction vessel 200 is configured to support nitrogen purging to eliminate or at least ameliorate the risk of accidental ignition. Some extraction vessel embodiments may additionally include a relief valve (e.g., relief valve 514 in FIG. 5) to vent explosive energy away from the human system operators and other equipment. In embodiments that do not utilize flammable process solvents, the extraction vessel 200 can instead be configured to withstand a comparatively lower working pressure of about 15 psi.

In operation, the first door 208a can be opened to facilitate insertion of harvested biomass into the extraction vessel 200 and/or removal of processed biomass from the extraction vessel 200. Further, the second door 208b can be opened to facilitate insertion of harvested biomass into the extraction vessel 200 and/or removal of processed biomass from the extraction vessel 200.

In some embodiments, the first door 208a and the second door 208b enable harvested biomass to be inserted into the extraction vessel 200 via the first door 208a and processed biomass to be removed from the extraction vessel 200 via the second door 208b (or vice versa) in an assembly line fashion. For example, and as mentioned earlier, in some embodiments, the extraction vessel 200 is configured to operate with a speedloader positioned at the ingress to the extraction vessel 200 and a discharge gantry positioned at the egress to the extraction vessel 200.

Figure 6A:
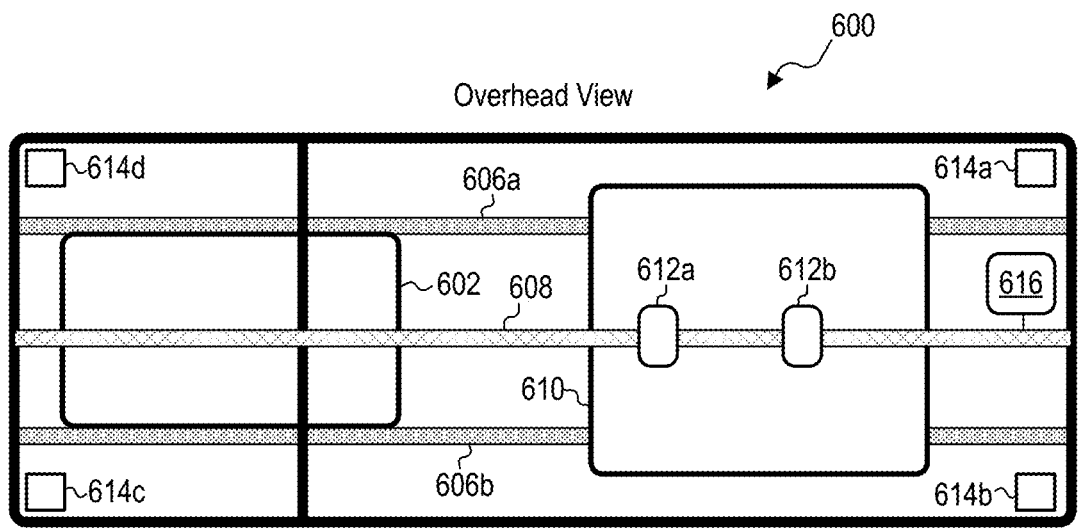
FIG. 6A shows an overhead cutaway view of an example speedloader/discharge gantry used in connection with extracting organic compounds from biomass according to some embodiments.
Figure 6B:
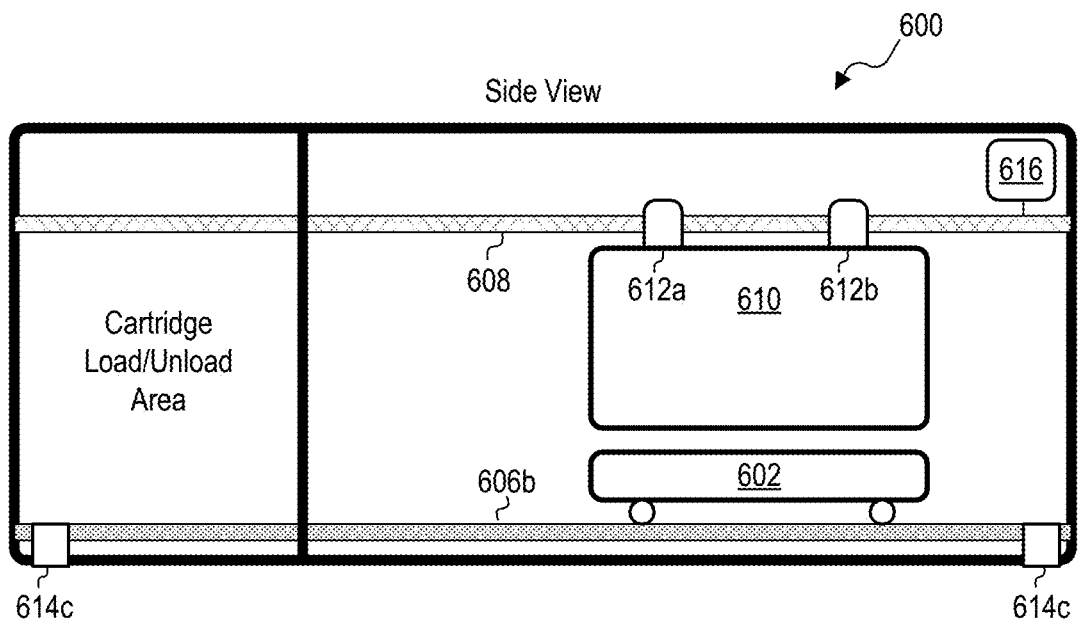
FIG. 6B shows a side cutaway view of an example speedloader/discharge gantry used in connection with extracting organic compounds from biomass according to some embodiments.

In operation, a cartridge 800 (FIGS. 8A and 8B) containing harvested biomass is loaded into a speedloader 600 (FIGS. 6A and 6B) positioned at the first door 208a of the extraction vessel 200. The speedloader 600 is equipped with a monorail system that includes a speedloader monorail 608 (FIGS. 6A and 6B). When the first door 208a is opened, the speedloader monorail 608 is configured to couple to the extraction vessel monorail 214 extending through the interior space 206 of the extraction vessel 200.

In this manner, the speedloader 600 comprises a speedloader monorail 608 extending through a substantial portion of an interior space of the speedloader 600 and configured to couple to the extraction vessel monorail 214 extending through an interior space 206 of the extraction vessel 214 to form a substantially continuous speedloader-to-extraction-vessel monorail system (the combination of monorail 608 and monorail 214), where the speedloader-to-extraction-vessel monorail system is configured to transport one or more cartridges 800 attached to the speedloader-to-extraction-vessel monorail system and containing harvested biomass from the speedloader 600 to the extraction vessel 200 for processing.

When the speedloader monorail 608 is coupled to the extraction vessel monorail 214, a cartridge 800 containing harvested biomass can be transferred from the speedloader 600 into the extraction vessel 200 along the monorail apparatus formed from the coupling of the speedloader monorail 608 with the extraction vessel monorail 214. In some embodiments, the monorail system of the speedloader 600 additionally includes a monorail drive 616 (FIGS. 6A and 6B) configured to move cartridges along the monorail.

Similarly, the discharge gantry 600 also comprises a discharge gantry monorail 608 extending through a substantial portion of an interior space of the discharge gantry 600 and configured to couple to the extraction vessel monorail 214 extending through the interior space 206 of the extraction vessel 200 to form a substantially continuous extraction-vessel-to-discharge-gantry monorail system (the combination of monorail 214 and monorail 608), where the extraction-vessel-to-discharge-gantry monorail system is configured to transport one or more cartridges 800 attached to the extraction-vessel-to-discharge-gantry monorail system and containing processed biomass from the extraction vessel 200 to the discharge gantry 600.

FIG. 2C shows the side cut-away view of FIG. 2A and the end cut-away view of FIG. 2B with the extraction vessel containing a cartridge 800 configured to hold biomass according to some embodiments. The side cut-away view shows cartridge 800 attached to the extraction vessel monorail 214 within the extraction vessel via cartridge couplers 802a and 802b. The end cut-away view shows an end view of the cartridge 800 attached to the extraction vessel monorail 214.

In some embodiments, movement of a cartridge 800 containing harvested biomass from the speedloader 600 through the interior space 206 of the extraction vessel 200 is further facilitated by cart track 216 extending along the bottom of the interior space 206 of the extraction vessel 200. For example, in some scenarios, a cartridge 800 attached to the extraction vessel monorail 214 within the extraction vessel 200 may additionally be at least partially supported at the bottom by a wheeled cart (or other suitable wheeled structure) (not shown) that is configured to roll along the cart track 216 extending along the bottom of the interior space 206 of the extraction vessel 200.

Returning to FIG. 2A, after one or more cartridges 800 containing harvested biomass have been placed into the extraction vessel 200, the doors 208a and 208b are closed and the extraction vessel 200 is sealed. Then, vacuum pump 222 connected to the extraction vessel 200 creates a vacuum within the interior space 206 of the extraction vessel 200. The vacuum may be a partial or a full vacuum. In some embodiments, the vacuum is about 28 Hg.

After drawing the vacuum within the interior space 206, process solvent obtained from one or more process solvent storage tanks 220 is applied to the harvested biomass contained in the one or more cartridges within the extraction vessel 200. The process solvent is routed from the process solvent storage tanks 220 to the nozzles 218a-f via a process solvent manifold 232. FIG. 2B shows a logical implementation of the process solvent manifold 232 routed from the one or more process solvent storage tanks 220 to the nozzles for illustration purposes. In a physical implementation, the hoses and/or piping of the process solvent manifold 232 would be routed along the outer surface of the extraction vessel 200, along the surface of the inner walls of the extraction vessel 200, and/or within the walls of the extraction vessel 200.

In operation, the process solvent is applied to the biomass within the extraction vessel 200 via a set of nozzles 218a-f. The example in FIG. 2A shows six nozzles for illustration purposes. In operation, embodiments may have more or fewer than six nozzles. The set of nozzles 218a-f may be arranged in any suitable configuration sufficient to apply process solvent to harvested biomass within the extraction vessel 200, such as, for example, a single row at or near the top of the extraction vessel 200, dual rows at or near the top of the extraction vessel 200 (e.g., as shown in FIG. 2B), rows along or near a meridian line of the extraction vessel 200, in rows at or near the bottom of the extraction vessel 200, or any combination thereof or any other suitable configuration.

Applying the process solvent to the harvested biomass via the set of nozzles 218a-f is sometimes referred to herein as "washing" the harvested biomass with process solvent.

In some embodiments, washing the harvested biomass within the extraction vessel 200 includes applying the process solvent in a vaporized form. In operation, maintaining the vacuum within the extraction vessel 200 while applying the process solvent helps to keep the process solvent in vaporized form. In some instances, at least some (and preferably most) of the process solvent is in a vaporized form. However, the process solvent is effective in liquid form as well.

Some embodiments may include more than one washing cycle. For example, some embodiments may include two, three, or more applications of the process solvent. Some embodiments may also include a liquid wash cycle (e.g., a higher air pressure within the extraction vessel 200) and a vapor wash cycle (e.g., at a lower air pressure within the extraction vessel).

Applying the process solvent to the harvested biomass causes at least some of the desired organic compound within the harvested biomass to separate from the harvested biomass, thereby resulting in (i) an extract and (ii) processed biomass. The extract at this stage includes the desired organic compounds and process solvent, and the processed biomass at this stage includes some residual process solvent.

Any process solvent suitable for extracting the one or more desired organic compounds from the harvested biomass may be used. For example, in some embodiments, the process solvent includes any one (or more) of (i) 1,1,2 Trans-dichloroethylene, (ii) Pinatec 5 TDCE™, (iii) 1,1,2 Trans-dichloroethylene R1234yf (2,3,3,3-Tetrafluoropropene), (iv) R134a (1,1,1,2-Tetrafluoroethane), (v) R-32 (Difluoromethane), (vi) R-125 (Pentafluoroethane), (vii) R441A (blend of ethane, propane, butane and isobutane/Hexafluoroethane), (viii) 1336mzz-z (cis-1,1,1,4,4,4-hexafluorobut-2-ene); (ix) t-DCE (trans-dichloroethylene), (ix) a blend comprising 70 wt. % or more of trans-1,2-dichloroethylene (t-DCE) 0.1 to about 30 wt. % of one or more of hydrofluoroether (HFE) and n-propyl bromide, (x) a blend comprising 1,1,2,2-tetrafluoroethyl-2,2,2-trifluoroethyl ether (R347), trans-1,2-dichloroethylene (tDCE) and a C-alcohol (ROH), wherein an amount of (R347) is from 25.0 to 75.0% by mass, an amount of (tDCE) is from 15.0 to 74.9% by mass and an amount of (ROH) is from 0.1 to 10.0% by mass, to a total amount of (R347), (tDCE) and (ROH), (xi) a blend comprising Solvokane™ X from Solvay corporation, (xii) a blend comprising Novec™ from 3M corporation, (xiii) a blend comprising Precision-V Solvent™ from Techspray, or (xiv) a blend comprising BestSolv™ from Best Technology.

After applying the process solvent, the vacuum is released and the extraction vessel 200 is returned to atmospheric pressure, thereby causing the extract to transition from a vapor form to a liquid form. The liquified extract collects along the slanted floor plate 226 (sometimes referred to as a winterization tray) at the bottom of the extraction vessel 200. In some embodiments, the floor plate 226 is removable for cleaning and maintenance.

After accumulating liquid extract in the bottom of the extraction vessel 200, some embodiments additionally include a winterization step. For example, after returning the extraction vessel 200 to atmospheric pressure, the liquid extract collected in the bottom of the extraction vessel 200 is cooled to a temperature sufficient to precipitate undesirable solids from the liquid extract. The undesirable solids in this instance include fats, waxes, lipids, and other inactive compounds contained within the liquid extract.

In some embodiments, cooling the accumulated liquid extract is facilitated at least in part by using the vacuum pump 222 to draw a vacuum again within the interior space 206 of the extraction vessel 200. In some embodiments, cooling the accumulated liquid extract is additionally or alternatively facilitated at least in part by circulating refrigerant through a jacket 234 (FIG. 2B) surrounding the extraction vessel 200, thereby lowering the temperature within the extraction vessel.

In some embodiments, the temperature within the extraction vessel 200 is reduced to approximately −20° F. or below. In some embodiments, the temperature within the extraction vessel 200 is reduced to below approximately −50° F., such as less than −50° F. or less than −60° F. In some embodiments, the liquid extract is reduced to a temperature of between approximately-20° F. and approximately −50° F.

The slanted floor plate 226 directs the liquid extract into a filter box 228 at or near the bottom of the extraction vessel. The filter box 228 contains one or more filters configured to allow the liquid extract to pass through while trapping the precipitated undesirable solids. The liquid extract that has passed through the filter box 228 is sometimes referred to herein as "filtered liquid extract" or simply "filtered extract." However, as mentioned elsewhere, the winterization step is optional. Liquid extract that has not been winterized (i.e., cooled and filtered) is sometimes referred to herein as "unfiltered liquid extract" or simply "unfiltered extract." In some embodiments, the filter box 228 inside of the extraction vessel 200. In some embodiments, the filter box 228 is outside of the extraction vessel 200.

Figure 7:
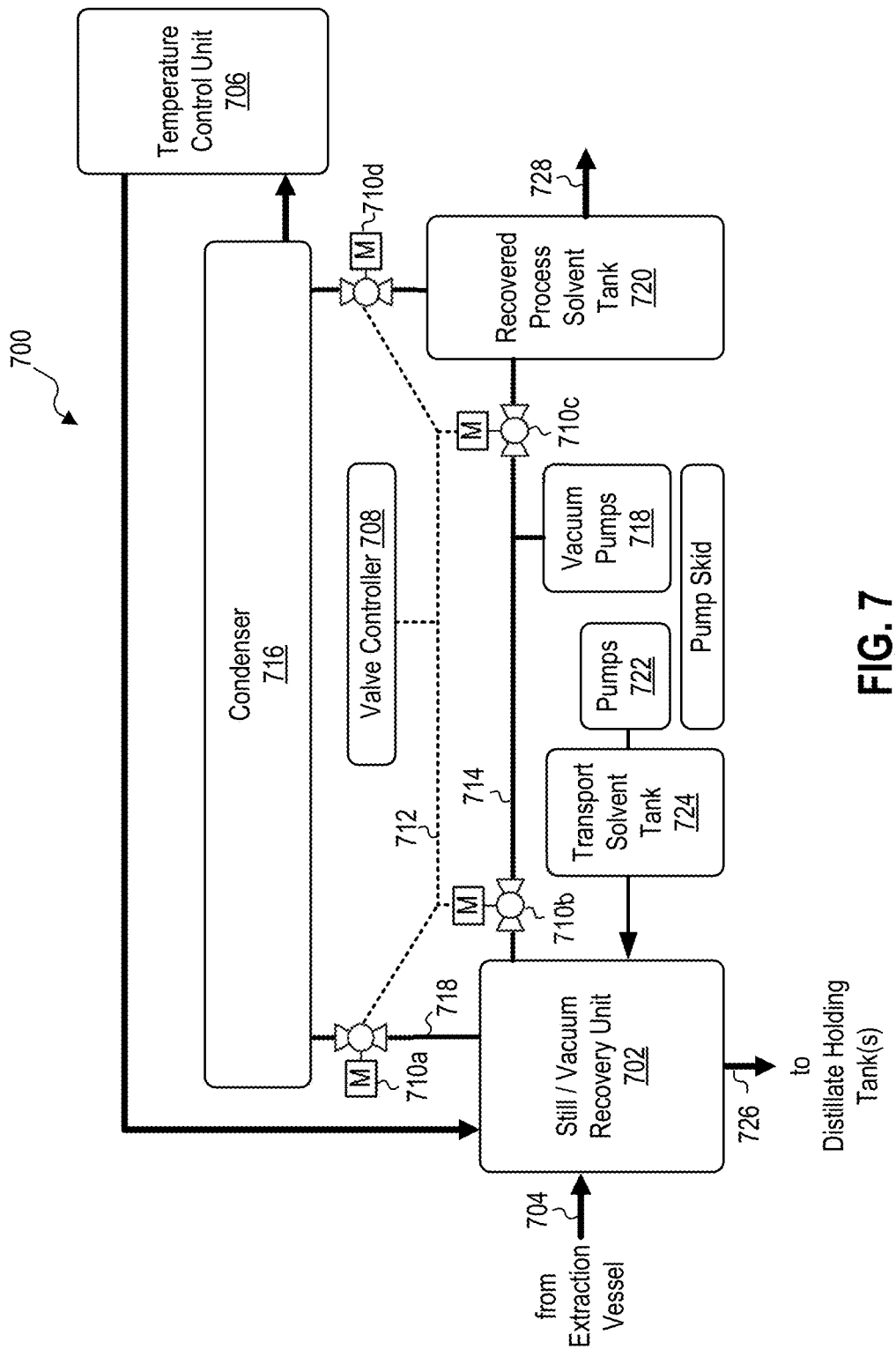
FIG. 7 shows an example distillery system used in connection with extracting organic compounds from biomass according to some embodiments.

The extraction vessel 200 includes an extraction vessel outlet 230 at the bottom via which the liquid extract (filtered or unfiltered) can be removed from the extraction vessel 200. In some embodiments, a pipe, tube, hose, or similarly suitable structure is attached to the extraction vessel outlet 230, and the liquid extract is routed (e.g., via a pump) from the bottom of the extraction vessel 200 to a distillery system (FIG. 7). Aspects of the distillation process are described further with reference to FIG. 7.

The processed biomass remaining in the extraction vessel 200 after the liquid extract has been moved from the extraction vessel 200 to the distillery system (FIG. 7) will typically contain residual process solvent. As mentioned previously, it is desirable in some instances to remove/recover this residual process solvent from the processed biomass. Some extraction vessel embodiments are configured to use the vacuum pump 222, a light source 240, and a fan 242 in connection with removing/recovering this residual process solvent from the processed biomass.

First, the residual process solvent (or at least some of the residual process solvent) within the processed biomass is evaporated by one or both of (i) using the vacuum pump 222 to lower the air pressure within the extraction vessel 200 and (ii) using the light source 240 to apply light to the processed biomass. In some embodiments, the light source 240 includes an array of lights that are arranged to apply light consistent with natural sunlight (including visible light, ultraviolet, and infrared wavelengths) to the processed biomass.

In operation, lowering the air pressure within the extraction vessel 200 reduces the air pressure on the surface of the processed biomass, which tends to make it easier for the residual process solvent to evaporate from the processed biomass. Further, as the molecules of the residual process solvent absorb the light emitted from light source 240, the molecules tend to experience an increase in heat, which enables them to gain sufficient energy to transition from the liquid phase to the gaseous phase.

Figure 5:
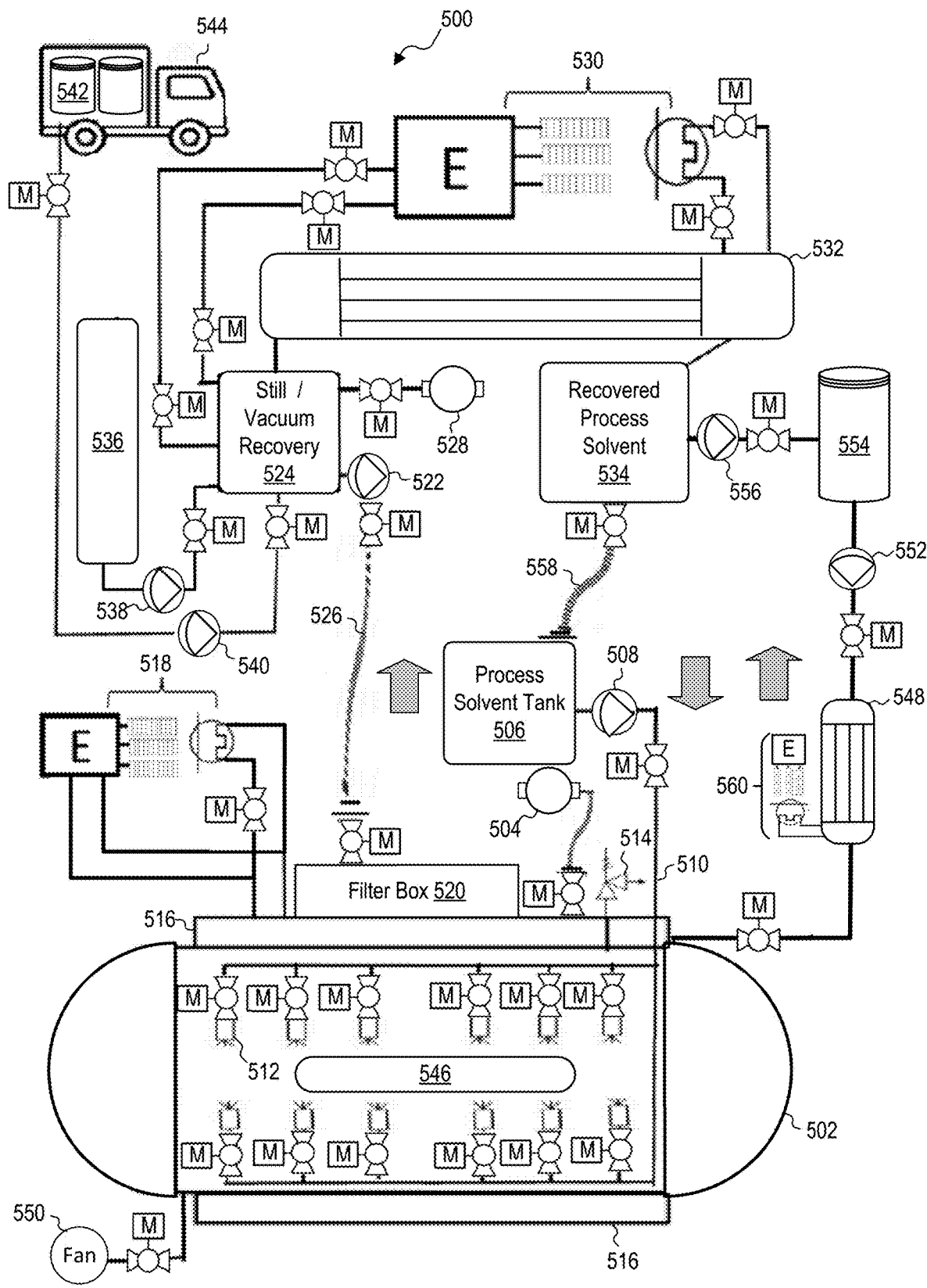
FIG. 5 shows an example piping and instrumentation diagram detailing aspects of a system for extracting organic compounds from biomass according to some embodiments.

After evaporating the residual process solvent, the fan 242 (or other suitable air source) blows air within the extraction vessel 200 containing the evaporated process solvent out of the extraction vessel 200 and into a process solvent reclamation condenser (FIG. 5). In operation, the process solvent reclamation condenser is configured to convert the evaporated process solvent back into a liquid form so that the recovered process solvent can be either be used again or disposed of.

Reclaiming the residual process solvent is an optional step. Some embodiments may implement the residual process solvent reclamation procedure, whereas other embodiments may not.

Next, the processed biomass (with or without residual process solvent) is removed from the extraction vessel 200. In some embodiments, removal of the processed biomass from the extraction vessel 200 is facilitated by a discharge gantry 600 (FIGS. 6A and 6B). As explained with reference to FIGS. 6A and 6B, the discharge gantry and the speedloader are the same (or substantially the same) apparatus, but the apparatus is referred to as a speedloader when used to load harvested biomass into the extraction vessel 200, and the apparatus is referred to as a discharge gantry when used to remove processed biomass from the extraction vessel 200.

In operation, a discharge gantry 600 (FIGS. 6A and 6B) is positioned at the second door 208*b* of the extraction vessel 200. The discharge gantry 600 is equipped with a monorail system that includes a discharge gantry monorail 608 (FIGS. 6A and 6B). When the second door 208*b* is opened, the discharge gantry monorail 608 is configured to couple to the extraction vessel monorail 214 extending through the interior space 206 of the extraction vessel 200.

When the discharge gantry monorail 608 is coupled to the extraction vessel monorail 214, a cartridge 800 containing processed biomass can be transferred from the extraction vessel 200 to the discharge gantry 600 along the monorail apparatus formed from the coupling of the discharge gantry monorail 608 with the extraction vessel monorail 214. In some embodiments, the monorail system of the discharge gantry 600 additionally includes a monorail drive 616 (FIGS. 6A and 6B) configured to move cartridges along the monorail.

Some embodiments also include an instrument and control panel 250, sometimes referred to herein as a control panel 250 (FIG. 2B). The control panel 250 may be placed anywhere on or near the extraction vessel 200. In operation, the control panel 250 is configured to collect data from various sensors, e.g., temperature sensors, pressure sensors, flow-rate sensors, contact sensors, humidity sensors, cameras, and any other type of sensor now known or later developed that is suitable for monitoring and/or controlling aspects of the disclosed processes. In some embodiments, the control panel 250 additionally includes controls for activating/deactivating and/or otherwise controlling various functions relating to implementing the disclosed processes, e.g., activating/controlling the vacuum pump 222, fan 242, light source 240, application of the process solvent via the nozzles 21*a-f*, the heating/cooling source controlling the temperature inside the extraction vessel 200, and/or other functions disclosed herein.

III. Biomass Harvesting and Preparation for Processing

FIG. 3 shows aspects of harvesting and preparing biomass for processing according to some embodiments. The biomass may be any type of plant containing oils or other desirable organic compounds that can be extracted from the plant via the disclosed extraction and distillation processes. In some embodiments, the plant is a *cannabis* plant. All phenotypes of *cannabis* may be utilized. Other plant materials and other organic biomass may be utilized as well without departing from the concepts disclosed herein. Other plants that may be used include tobacco, palm nuts, almonds, or other plants containing desirable oils.

For embodiments utilizing THC-based *cannabis* plants, the structure of the harvested plant generally grows out horizontally then curls upwards to produce flowering colas. Traditional hemp plant may also be used, which has a structure similar to bamboo with the plants producing flowering colas at an angle of 45 degrees. The traditional hemp architecture facilitates long fiber production which can be desirable when using the processed biomass for making rope and rigging. As such, using plants having such architecture could facilitate secondary usage of the processed biomass after processing as it offers more product capabilities upon reclamation. However, hemp phenotypes having different architectures yielding shorter fibers may also be used.

Figure 4:
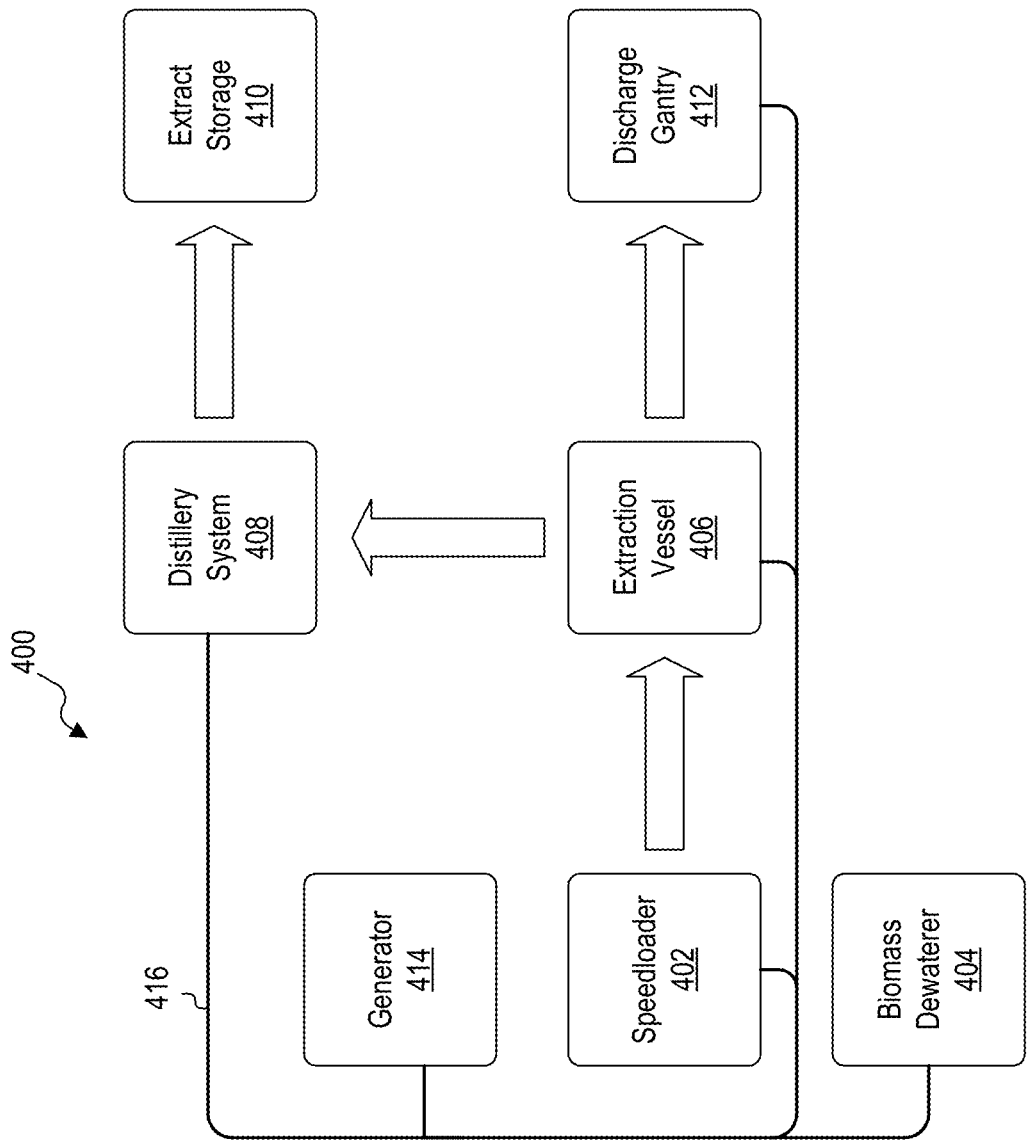
FIG. 4 shows an example mobile extraction site layout according to some embodiments, which can be containerized to facilitate movement to different infield sites.

As mentioned earlier, wet or dry plants can be harvested and used with the disclosed extraction vessel and distillery system. There are known techniques for extracting organic compounds from dry biomass according to processes different from the disclosed processes. However, aspects of processing wet biomass are unique to the disclosed processes. In general, dry biomass promotes greater volumes of throughput during processing than wet feedstock because wet biomass tends to be much heavier than dry biomass. However, the capability of the disclosed processes to extract organic compounds from wet biomass is unique to the disclosed processes. Prior attempts to extract organic compounds from wet biomass have generally been unsuccessful. Using the disclosed processes to extract organic compounds from wet biomass is very important, as the disclosed processes are capable of processing sodden plants that have been wetted by unanticipated rainfall at the farm site or by other means of wetting the plants, which includes frozen plants that have been stock-piled. The disclosed embodiments can perform additional dewatering of the harvested plants, for example, allowing it to drain by gravity or by utilization of a biomass dewaterer 404 (FIG. 4).

A harvester 302 is used to harvest biomass 304 (e.g., plants) from a field 300. In some embodiments, the harvester 302 uses one or both of a stalk cutter 308 to cut the biomass 304 and/or a baler 306 to grasp the biomass 304.

In some scenarios, the harvester 302 places one or more whole plants 314 into a cartridge 800 (FIGS. 8A and 8B). In some scenarios, the harvester 302 places a plant 304 into a bucking machine 310 configured to buck the plant. The bucked plant 316 is then transported via a conveyor 312 to a cartridge 800. In some scenarios, a cartridge 800 may contain both whole plants 314 and bucked plants 316. For example, in embodiments where the plant is a *cannabis* plant, the biomass may include individual colas, flower branches, or the entire *cannabis* plant structure.

The cartridge 800 may take any suitable form sufficient to accommodate whole and/or bucked plants for processing within an extraction vessel (FIGS. 2A-C). The example cartridge 800 depicted in FIGS. 8A and 8B is a cage-like metal enclosure. However, in other examples, the cartridge 800 may be a plastic or plastic/metal composite enclosure or cage structure, a bag, a harness, or any other structure now known or later developed that is sufficient for accommodating whole plants 314 and/or bucked plants 316 for processing by the disclosed systems according to the disclosed methods.

In some embodiments, the entire *cannabis* plant can be unearthed from the field and placed directly into a cartridge 800. In some instances, an entire plant structure except the root ball may be placed into a cartridge 800. The root ball contains compounds that can be extracted, but processing the root ball may require additional filtration because of the soil contamination. Nevertheless, in embodiments where the root ball is processed with the rest of the plant, specialized filtration can be included in the extraction vessel, e.g., with an additional filtration step or with additional filters integrated within the filter box of the extraction vessel (e.g., filter box 228 in FIGS. 2A-C).

In some instances, the harvester 302 can bind a whole plant with the baler 306 to reduce the circumference size, and cut the stalk of the plant 304 with the stalk cutter 308 for removal. In some embodiments, the plant can be bucked with the bucking machine 310 to remove the limbs of the plants from the stalks or remove the individual colas from the branches. Some embodiments may also utilize individual trichomes from the *cannabis* plants which may have been removed from the plant structure.

As described elsewhere herein, the cartridge 800 can be placed into a speedloader (FIGS. 6A and 6B) that is configured to load the cartridge 800 containing the biomass (i.e., whole plant 314 and/or bucked plant 316) into the extraction vessel 200 (FIGS. 2A-2C) for processing.

In some embodiments, information about the field 300 and/or details about the biomass 304 are collected when the biomass 304 is harvested. In some examples, the system records and/or tracks the time and location of each individual plant via any one or more of tagging, GPS, color coding of the bailing twine, RFID, scan, barcode, image recognition, and so on. This information can later be associated with distillate obtained from the biomass 304.

IV. Mobile Extraction Site Layout

FIG. 4 shows an example mobile extraction site layout 400 according to some embodiments, which can be containerized to facilitate movement to different infield sites. In particular, the components shown in FIG. 4 can be loaded onto a truck, carried to a harvest location, deployed "infield" at the harvest location, used at the harvest location to extract and distill organic compounds from the harvested biomass, and then packed back onto the truck and carried to another harvest location.

The mobile extraction site layout 400 includes a speedloader 402, extraction vessel 406, distillery system 408, extract storage 410, discharge gantry 412, and generator 414.

The speedloader 402, extraction vessel 406, distillery system 408, and discharge gantry 412 components are the same as or substantially the same as the speedloader/discharge gantry 600 (FIGS. 6A and 6B), extraction vessel 200 (FIGS. 2A-C), distillery system 700 (FIG. 7) described elsewhere herein.

Some embodiments additionally include a biomass dewaterer 404. The biomass dewaterer 404 is configured to remove water from harvested biomass before the harvested biomass is inserted into a cartridge 800 (FIGS. 8A and 8B) in whole plant or bucked plant form.

The generator 414 is configured to provide electrical power to the speedloader 402, biomass dewaterer 404, extraction vessel 406, distillery system 408, and discharge gantry 412 via power distribution system 416. In operation, the components of the mobile extraction site layout 400 can be carried to and deployed in a field (e.g., field 300 in FIG. 3) where biomass is being harvested.

Any quantity or volume of plants may be harvested and processed with the configuration shown in FIG. 4. In some embodiments, the components of FIG. 4 can be configured to (i) process one thousand pounds of dry biomass per cycle, and/or (ii) process four thousand pounds of wet biomass per cycle. Since wet biomass comprises approximately 70-75% water whereas dry biomass has had the water removed, the four thousand pounds of wet biomass and one thousand pounds of dry biomass correspond to about the same amount of biomass.

V. Example Piping and Instrumentation Diagram

FIG. 5 shows an example piping and instrumentation diagram (PID) 500 detailing aspects of a system for extracting organic compounds from biomass according to some embodiments. The purposed of the PID 500 is to show how extract and process solvent are routed between and among the components of the extraction system disclosed herein. For ease of illustration, certain details of the individual components shown in the PID 500 that are described elsewhere herein are not repeated in the context of the PID 500.

Harvested biomass is placed within an extraction vessel 502. After the harvested biomass has been placed within the extraction vessel 502, the extraction vessel 502 is sealed. A vacuum pump 504 connected to the extraction vessel 502 is configured to draw a vacuum inside the extraction vessel 502.

While the extraction vessel 502 is under vacuum, the biomass within the extraction vessel 502 is washed with process solvent from process solvent tank 506. In operation, pump 508 pumps the process solvent from process solvent tank 506 to the extraction vessel 502 via one or more hoses 510 (or pipes, or similar structure sufficient to route liquid from one location to another.

The extraction vessel 502 includes an array of nozzles 512 configured to wash the biomass contained with the extraction vessel 502 with process solvent obtained from the process solvent tank 506. At least some of the process solvent from the nozzles 512 is in vaporized form. However, in some instance, some of the process solvent may be in vapor form and some may be in liquid form. Washing the biomass with the process solvent extracts the desired organic compounds from the biomass, thereby resulting in (i) an extract comprising the desired organic compound and the process solvent and (ii) processed biomass. The processed biomass includes residual process solvent entrained therein.

After washing the biomass with process solvent, the vacuum is released and the extraction vessel 502 is returned to atmospheric pressure. Returning the extraction vessel 502 to atmospheric pressure causes the extract to transition from vapor to liquid phase. The liquid extract collects on the bottom of the extraction vessel 502.

As explained earlier, winterization is an optional procedure. Some scenarios that include winterization include (i) re-sealing the extraction vessel 502 and using the vacuum pump 504 to draw another vacuum within the extraction vessel 502, and (ii) circulating refrigerant through a jacket 516 surrounding the extraction vessel 502. Temperature unit 518 is configured to send the refrigerant to the jacket 516 and extract heat from circulated refrigerant returning from the jacket 516. The PID figure shows two 516 reference numbers because both reference numbers correspond to the same jacket 516. The cutaway view shows a portion of the jacket 516 at the top of the extraction vessel 502 and a portion of the jacket 516 at the bottom of the extraction vessel 502.

Drawing the vacuum and lowering the temperature within the extraction vessel 502 precipitates undesirable solids contained within the liquid extract collected at the bottom of the extraction vessel. The liquid extract is routed through the filter box 520 to remove any residual undesirable solids. The extract at this stage is sometimes referred to as filtered liquid extract or simply filtered extract.

Next, pump 522 is used to pump the filtered extract from the extraction vessel 502 to the still 524 via hose 526 (or pipe or other structure suitable for conveying liquids).

In embodiments that do not include winterization, the liquid extract collected at the bottom of the extraction vessel 502 is sent to the still 524 without winterization. Unwinterized extract is sometimes referred to as unfiltered liquid extract or simply unfiltered extract. In such embodiments, pump 522 is used to pump the unfiltered extract from the extraction vessel 502 to the still 524 via hose 526.

Next, the liquid extract (filtered or unfiltered) within the still 524 is distilled to separate process solvent within the liquid extract from the desired organic compounds within the liquid extract.

In some embodiments, the still 524 is a vacuum still that is configured to lower the air pressure within the still 524 to lower the boiling point of the process solvent. However, in other embodiments, the still 524 is a traditional (non-vacuum) still.

In such vacuum still configurations, vacuum pump 528 is used to draw a vacuum within the still 524. And heat from the temperature unit 530 is used to heat the liquid extract within the still 524, thereby boiling off the process solvent contained with the liquid extract. Air containing the boiled off process solvent is routed to condenser 532, which converts the process solvent back into liquid form where it is collected in recovered process solvent tank 534.

In traditional still configurations, heat from the temperature unit 530 is used to heat the liquid extract within the still 524, thereby boiling off the process solvent contained with the liquid extract. Air containing the boiled off process solvent is routed to condenser 532, which converts the process solvent back into liquid form where it is collected in recovered process solvent tank 534.

Boiling off the process solvent within the still 524 creates a thick, viscous distillate that includes the desired organic compounds. Transport solvent from a transport solvent storage tank 536 is pumped (via pump 538) into the still 524 and mixed with the thick, viscous distillate, thereby creating a reduced-viscosity distillate. Pump 540 is then used to pump the reduced-viscosity distillate from the still 524 to one or more distillate storage tanks 542 where truck 544 can transport the distillate away from the field for further processing, storage, and/or distribution.

Back in the extraction vessel 502, the processed biomass containing the residual process solvent can be further processed to remove the process solvent. In operation, the residual process solvent contained within the processed biomass is evaporated to generate air containing the evaporated process solvent by one or both (i) using the vacuum pump 504 to draw a vacuum within the extraction vessel 502, and (ii) applying light to the processed biomass within the extraction vessel 502 via light sources 546 contained within the extraction vessel 502.

Next the air within the extraction vessel 502 containing the evaporated process solvent is directed out of the extraction vessel 502 and into a process solvent reclamation condenser 548. In operation, fan 550 (or another source of air) is operated to blow the air containing the evaporated process solvent out of the extraction vessel 502 and into the process solvent reclamation condenser 548.

The process solvent reclamation condenser 548 is configured to condense the residual process solvent from the air containing the evaporated residual process solvent, resulting in liquid residual process solvent.

In operation, temperature control unit 560 connected to the process solvent reclamation condenser 548 controls the temperature of the process solvent reclamation condenser 548 to cause condensation of the evaporated residual process solvent, e.g., by cooling the air containing the evaporated residual process solvent to a temperature sufficient to cause condensation. In some embodiments, the temperature control unit 560 may additionally or alternatively heat the air containing the evaporated residual process solvent within the process solvent reclamation condenser 548 in certain scenarios.

Pump 552 is arranged to pump the liquid residual process solvent from the process solvent reclamation condenser 548 to a reclaimed process solvent storage tank 554. The reclaimed process solvent in the reclaimed process solvent storage tank 554 can then be pumped (via pump 556) into the recovered process solvent tank 534 and combined with the recovered process solvent in the recovered process solvent tank 534 from the distillation process. The process solvent within the recovered process solvent tank 534 can then be transported via hose 558 to the process solvent tank 506 and used again.

VI. Speedloader/Discharge Gantry

FIG. 6A shows an overhead cutaway view of an example speedloader/discharge gantry 600 used in connection with extracting organic compounds from biomass according to some embodiments. FIG. 6B shows a side cutaway view of an example speedloader/discharge gantry 600 used in connection with extracting organic compounds from biomass according to some embodiments.

As described earlier, the speedloader and the discharge gantry are essentially the same apparatus, but the apparatus is referred to as a speedloader when it is used to load harvested biomass into the extraction chamber and as a discharge gantry when it used to remove processed biomass from the extraction chamber. In operation, and as illustrated in FIG. 4, a typical implementation includes a speedloader at the ingress to the extraction chamber and a discharge gantry at the egress to the extraction chamber.

The speedloader/discharge gantry 600 includes a speedloader monorail 608 that is configured to couple to a extraction vessel monorail (e.g., extraction vessel monorail 214 in FIGS. 2A-2C) that runs through the interior of the extraction chamber. When the speedloader monorail 608 is coupled to the extraction chamber monorail (e.g., monorail 214), a cartridge 610 attached to the speedloader monorail 608 via cartridge couplers 612a and 612b can be routed from the speedloader 600 into the extraction vessel via the combined monorail structure formed by the speedloader monorail and the extraction vessel monorail. And when the discharge gantry monorail 608 is coupled to the extraction chamber monorail (e.g., monorail 214), a cartridge 610 attached to the extraction chamber monorail (e.g., monorail 214) via cartridge couplers 612a and 612b can be routed from the extraction chamber and into the discharge gantry 600 via the combined monorail structure formed by the extraction vessel monorail and the discharge gantry monorail.

In some embodiments, the speedloader/discharge gantry 600 includes a cart 602 that rolls along cart tracks 606a, 606b within the speedloader/discharge gantry 600. The cart 602 is used for attaching cartridges 610 to the speedloader monorail 608 and removing cartridges 610 containing processed biomass from discharge gantry monorail 608.

For example, a cartridge 610 containing harvested biomass can be placed onto the cart 602 in the cartridge loading area of the speedloader 600, and the cart can be used to help properly position the cartridge couplers 612a, 612b under the speedloader monorail 608 to facilitate secure attachment of the cartridge 610 to the speedloader monorail 608.

Similarly, the cart 602 can be placed under a cartridge 610 containing processed biomass within the discharge gantry 600 so that once the cartridge 610 containing the processed biomass has been detached from the discharge gantry monorail 608, the cartridge 610 can be rolled (via the cart 602) along the cart tracks 606a, 606b to the cartridge unload area of the discharge gantry 600.

In some embodiments, the monorail 608 of the speedloader/discharge gantry 600 includes a monorail drive 616 that is configured to move cartridges 610 along the monorail 608. For example, the monorail drive 616 in the speedloader 600 is configured to move cartridges 610 along the monorail 608 from the speedloader 600 to the extraction vessel. And the monorail drive 616 in the discharge gantry 600 is configured to move cartridges 610 along the monorail 608 from the extraction vessel and into the discharge gantry 600.

In some embodiments, the speedloader/discharge gantry 600 includes leveling pylons 614a-614d that can be adjusted to help align the monorail 608 in the speedloader/discharge gantry 600 with the extraction chamber monorail (e.g., extraction vessel monorail 214) to facilitate the coupling of the monorail 608 with extraction vessel monorail 214.

VII. Distillery System

FIG. 7 shows an example distillery system 700 used in connection with extracting organic compounds from biomass according to some embodiments.

The distillery system 700 includes, among other components, a still/vacuum recovery unit 702, a temperature control unit 706, a condenser 716, a set of valves 710a-d operated by a valve controller 708 connected to the valves via a control network 712, and a recovered process solvent tank 720 that operate in combination with each other and other components of the distillery system 700 to create a distillate from the liquid extract (filtered or unfiltered) received from an extraction vessel.

The still/vacuum recovery unit 702 may be a traditional still or a vacuum still. For ease of explanation, the description of FIG. 7 will refer to the still/vacuum recovery unit 702 as simply the still 702.

The still 702 includes an inlet 704 configured to receive liquid extract from an extraction vessel. The distillery system 700 uses heat from the temperature control unit 706 to heat the liquid extract within the still 702 to a temperature sufficient to boil off the process solvent contained within the liquid extract.

In embodiments where the still 702 is configured as a vacuum still, the valve controller 708 opens valve 710b (and keeps valves 710a, 710c, and 710d closed), and one or more vacuum pumps 718 extract air from the still 702 via pipe 714 to draw a vacuum within the still 702. Drawing a vacuum within the still 702 lowers the air pressure within the still 702, which in turn lowers the boiling point of the process solvent contained within the liquid extract. While the still 702 is under vacuum, the distillery system 700 uses heat from the temperature control unit 706 to heat the liquid extract within the still 702.

In some embodiments, the distillery system 700 is configured to heat the liquid extract within the still 702 to a temperature that is at least one of (i) between about 100° F. and about 130° F. or (ii) sufficient to boil the process solvent contained within the liquid extract. Recall that, for vacuum still embodiments, the boiling point of the process solvent is lower under vacuum than at normal atmospheric pressure. And in such configurations, the distillery system 700 is generally able to boil off the process solvent at a temperature lower than between about 100° F. and about 130° F., which is the temperature typically required to boil off the process solvent at normal atmospheric pressure.

In some embodiments, the distillery system 700 is configured to heat the liquid extract within the still 702 to a temperature that is at least one of (i) more than about 135° F. or (ii) sufficient to cause decarboxylation of the desired organic compound contained within the liquid extract.

The air containing the process solvent that has been boiled off from the liquid extract is routed to the condenser 716 via pipe 718. The temperature control unit 706 cools the condenser 716, thereby causing the process solvent within the condenser 716 to condense back into liquid form where it can be collected in the recovered process solvent tank 720.

In some embodiments, the one or more vacuum pumps 718 are configured to operate in combination with valves 710a, 710c, and 710d to pull the air containing the boiled off process solvent from the still 702 and into (and through) the condenser 716. The valves 710a, 710c, and 710d are controlled via the valve controller 708 connected to the valves 710a, 710c, and 710d via the control network 712.

Once the liquid is heated in the still to a temperature sufficient to boil the process solvent, valve 710a is opened to allow the air containing the process solvent to flow into the condenser 716 via pipe 718. In some configurations, valves 710c and 710d can be opened to pull the vapor containing the process solvent through the condenser 716. The temperature control unit 706 is configured to cool the condenser 716 (or remove heat from the condenser 716) to cause the process solvent to condense into liquid form so that the liquid process solvent can be collected in the recovered process solvent tank 720. The recovered process solvent contained within the recovered process solvent tank 720 can be removed from the recovered process solvent tank 720 via an outlet 728.

Boiling off the process solvent within the still 702 results in a distillate containing the desired organic compound(s) from the liquid extract. As mentioned earlier, this distillate tends to be thick and viscous. So, to remove the distillate from the still 702, one or more pumps 722 pump transport solvent from a transport solvent tank 724 to the still 702 where the process solvent is mixed with the viscous distillate. In some embodiments, the still 702 is equipped with a mechanism (e.g., a mixer, agitator, circulator, or similar) configured to mix the process solvent with the viscous distillate. Adding and/or mixing the transport solvent to/with the distillate within the still 702 creates a reduced-viscosity distillate that can be pumped out of the still 702 via an outlet 726 to one or more distillate holding tanks. In some embodiments, the transport solvent is or at least includes ethanol. In some embodiments, the reduced-viscosity distillate includes between about 5% to 10% ethanol.

VIII. Material Handling Cartridge

FIG. 8A shows a front view of a material handling cartridge 800 used with a speedloader/discharge gantry and extraction vessel in connection with extracting organic compounds from biomass according to some embodiments. FIG. 8B shows an end view of a material handling cartridge 800 used with a speedloader/discharge gantry and extraction vessel in connection with extracting organic compounds from biomass according to some embodiments.

The material handling cartridge 800 (sometimes referred to simply as a cartridge) is configured to accommodate harvested biomass for processing within an extraction vessel as described herein.

The cartridge 800 has cartridge couplers 802a and 802b at the top of cartridge 800 that are configured to attach the cartridge 800 to the monorail within a speedloader/discharge gantry (e.g., monorail 608 in FIGS. 6A-B) and extraction vessel (e.g., monorail 214 in FIGS. 2A-C). Support components 804a and 804b are arranged to improve the structural integrity of the cartridge 800 and help the container accommodate heavy loads of harvested biomass. As mentioned earlier, the cartridge 800 can accommodate wet, dry, or frozen biomass. In some scenarios, wet biomass may include between 70-75% water by weight.

The cartridge 800 includes front-end-facing forklift pockets 806a and 806b (806b not shown), rear-end-facing forklift pockets 808a and 808b (808b not shown), and a set of side-facing forklift pockets 810a and 810b. The front-end-facing forklift pockets 806a and 806b (806b not shown) are configured to accept forks from a forklift in the direction of the arrow pointing toward the front-end-facing forklift pocket 806a. The rear-end-facing forklift pockets 808a and 808b (808b not shown) are configured to accept forks from a forklift in the direction of the arrow pointing toward the rear-end-facing forklift pocket 808a. And the side-facing forklift pockets 810a and 810b are configured to accept forks from a forklift in the direction of the arrows pointing toward the side-facing forklift pockets 810a and 810b.

The example cartridge 800 includes doors 812a and 812b configured in a slide down configuration. In operation, the doors 812a and 812b open by sliding down the outside of the cartridge 800 (as indicated by the arrow in FIG. 8B) to facilitate loading harvested biomass into the cartridge 800 and removing processed biomass from the cartridge 800. In other embodiments, the doors may instead be configured to swing open or to attach/detach. Any other suitable opening/closing arrangement could be used as well.

In some embodiments, the cartridge 800 takes the form of a metal cage that holds the biomass, thereby allowing the process solvent to be applied to the harvested biomass and allowing any liquid extract to fall from the cartridge 800 into the bottom of the extraction vessel. As mentioned earlier, the cartridge 800 may alternatively be a plastic or plastic/metal composite enclosure or cage structure, a bag, a harness, or any other structure now known or later developed that is sufficient for accommodating whole plants 314 and/or bucked plants 316 for processing by the disclosed systems according to the disclosed methods.

IX. Example Methods

Figure 9:
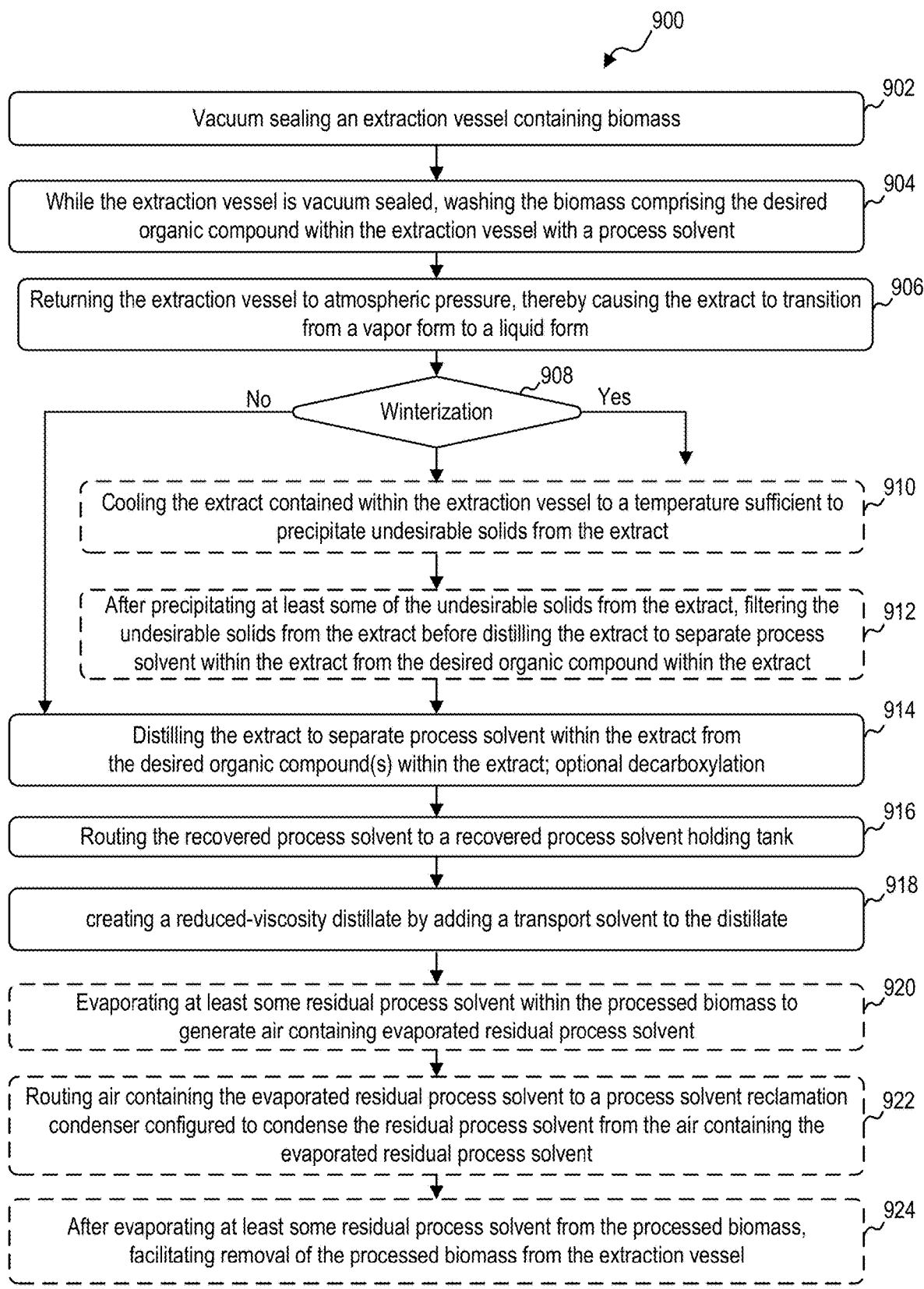
FIG. 9 shows an example method of extracting organic compounds from biomass according to some embodiments.

FIG. 9 shows an example method 900 of extracting organic compounds from biomass according to some embodiments.

Method 900 begins at block 902, which includes vacuum sealing an extraction vessel containing biomass, where the biomass includes one or more desired organic compounds. In some examples, vacuum sealing the extraction vessel containing the biomass at block 902 includes vacuum sealing the extraction vessel at a vacuum level of about 28 Hg. Partial vacuums may also be utilized based on vapor cloud density and condensation efficacy associated with different process solvents.

In some embodiments, the biomass includes (i) wet biomass having water content greater than about 70%, (ii) dry biomass, and/or (iii) frozen biomass. In some embodiments, the biomass includes a whole plant. In some embodiments, the biomass includes a processed plant, sometimes referred to as a bucked plant.

In some embodiments, the biomass includes *cannabis* and the desired organic compound(s) include delta-9-tetrahydrocannabinol (THC) and/or cannabidiol (CBD). In some embodiments, the biomass includes tobacco and the desired organic compound(s) includes nicotine.

Next, method 900 advances to block 904, which includes, while the extraction vessel is vacuum sealed, washing the biomass comprising the desired organic compound(s) within the extraction vessel with a process solvent. Some embodiments include washing the biomass comprising the desired organic compound within the extraction vessel with the process solvent via two or more washing cycles.

In some embodiments, at least some of the process solvent is in vaporized form. Introducing the process solvent in vacuum conditions allows the process solvent to vaporize and condense on all surfaces of the biomass that has been placed within the extraction vessel. Some embodiments may include washing the biomass with process solvent where some of the process solvent is in vapor form and some of the process solvent is in liquid form. Some embodiments may include both a liquid wash and a vapor wash cycle.

In operation, washing the biomass with the process solvent at block 904 causes at least some of the desired organic compound(s) within the biomass to separate from the biomass thereby resulting in (i) an extract comprising the desired organic compound and the process solvent and (ii) processed biomass, wherein the processed biomass comprises residual process solvent.

In some embodiments, the process solvent includes any one or more of (i) 1,1,2 Trans-dichloroethylene, (ii) Pinatec 5 TDCE™, (iii) 1,1,2 Trans-dichloroethylene R1234yf (2,3,3,3-Tetrafluoropropene), (iv) R134a (1,1,1,2-Tetrafluoroethane), (v) R-32 (Difluoromethane), (vi) R-125 (Pentafluoroethane), (vii) R441A (blend of ethane, propane, butane and isobutane/Hexafluoroethane), (viii) 1336mzz-z (cis-1,1,1,4,4,4-hexafluorobut-2-ene); (ix) t-DCE (trans-dichloroethylene), (ix) a blend comprising 70 wt. % or more of trans-1,2-dichloroethylene (t-DCE) 0.1 to about 30 wt. % of one or more of hydrofluoroether (HFE) and n-propyl bromide, (x) a blend comprising 1,1,2,2-tetrafluoroethyl-2,2,2-trifluoroethyl ether (R347), trans-1,2-dichloroethylene (tDCE) and a C-alcohol (ROH), wherein an amount of (R347) is from 25.0 to 75.0% by mass, an amount of (tDCE) is from 15.0 to 74.9% by mass, and an amount of (ROH) is from 0.1 to 10.0% by mass, to a total amount of (R347), (tDCE) and (ROH), (xi) a blend comprising Solvokane™ X from Solvay corporation, (xii) a blend comprising Novec™ from 3M corporation, (xiii) a blend comprising Precision-V Solvent™ from Techspray, or (xiv) a blend comprising Best-Solv™ from Best Technology.

Further potential alternative reagents could also be used, such as siloxane terpenes. Further, a propellant like $CO_2$ may additionally be used for smaller quantities, such as a mix of 75% t-DCE/10-25% HFE/remainder $CO_2$ or other inert gas. Perfluoromethyldecalin may also be utilized even though it tends to have a boiling point higher than some of the other above-listed solvents. However, Perfluoromethyldecalin has several benefits, including it being non-toxic, stable, non-reactive, and inert. Lastly, other fully saturated fluorinated nonflammable alkanes, such as Perflexane C6F14 may be used as well.

In some embodiments, 2-4 gallons of process solvent are utilized per cycle of harvested biomass through the process. Re-cycling the process solvent (e.g., via blocks 916 and 920-924 described below) can recover up to 99% of organic compounds without adding new process solvent. In some embodiments, the amount of process used when washing the biomass within the extraction vessel is between about a 35% to 45% ratio of process solvent to biomass. In some embodiments, the amount of process solvent used to wash the biomass is a ratio of about 40% process solvent to biomass. In some embodiments, the washing process of block of 904 includes using about 440 gallons of process solvent per 4,000 wet pounds of biomass.

Next, method 900 advances to block 906, which includes returning the extraction vessel to atmospheric pressure, thereby causing the extract to transition from a vapor form to a liquid form. This liquid extract falls to the bottom of the extraction vessel.

As described earlier, winterization is an optional step as indicated by block 908. For embodiments that includes winterization, method 900 advances to block 910 after block 908, and then continues to block 914 after block 912. But for embodiments that do not include winterization, method 900 skips blocks 910 and 912 and advances directly to block 914 after block 908.

After returning the extraction vessel to atmospheric pressure at block 906, block 910 includes cooling the extract contained within the extraction vessel to a temperature sufficient to precipitate undesirable solids from the extract. In some embodiments, cooling the extract contained within the extraction vessel to a temperature sufficient to precipitate at least some of the undesirable solids from the extract at block 910 includes cooling the extract to a temperature between about −20° F. to about −60° F. In some embodiments, cooling the extract contained within the extraction vessel to a temperature sufficient to precipitate at least some of the undesirable solids from the extract at block 910 additionally includes vacuum sealing the extraction vessel again and cooling the extract while the extraction vessel is vacuum sealed.

After precipitating at least some of the undesirable solids from the extract at block 910, block 912 includes filtering the undesirable solids from the extract before distilling the extract to separate process solvent within the extract from the desired organic compound within the extract.

After block 912 (or after block 908 for embodiments that do not include blocks 910 and 912, method 900 advances to block 914, which includes distilling the extract to separate process solvent within the extract from the desired organic compound within the extract, resulting in (i) recovered process solvent and (ii) a distillate comprising the desired organic compound.

In some embodiments, distilling the extract to separate process solvent within the extract from the desired organic compound within the extract at block 912 includes heating the extract to a temperature sufficient to boil the process solvent. In some embodiments, distilling the extract to separate process solvent within the extract from the desired organic compound within the extract at block 912 includes heating the extract to a temperature sufficient to cause decarboxylation of at least one desired organic compound within the extract. In some embodiments, distilling the extract to separate process solvent within the extract from the desired organic compound within the extract at block 912 includes heating the extract to a temperature of more than about 135° F.

Next, method 900 advances to block 916, which includes routing the recovered process solvent to a recovered process solvent holding tank.

Next, method 900 advances to block 918, which includes creating a reduced-viscosity distillate by adding a transport solvent to the distillate (and perhaps also mixing the transport solvent with the distillate). In some embodiments, the transport solvent is (or at least includes) ethanol. In some embodiments where the transport solvent is or includes ethanol, creating the reduced-viscosity distillate by adding and/or mixing the transport solvent to the distillate at block 918 includes adding ethanol to the distillate comprising the desired organic compound to generate a reduced-viscosity distillate comprising between about 5% to 10% ethanol. Some embodiments of block 918 additionally include routing the reduced-viscosity distillate to a distillate holding tank.

Some embodiments additionally include optional blocks 920-924.

Block 920 includes evaporating at least some residual process solvent within the processed biomass to generate air containing evaporated residual process solvent by one or both of (i) lowering air pressure within the extraction vessel containing the processed biomass and (ii) applying light to the processed biomass within the extraction vessel.

Next, block 922 includes routing air containing the evaporated residual process solvent to a process solvent reclamation condenser configured to condense the residual process solvent from the air containing the evaporated residual process solvent, resulting in liquid residual process solvent.

Next, block 924 includes after evaporating at least some residual process solvent from the processed biomass, facilitating removal of the processed biomass from the extraction vessel.

X. Conclusions

The above description of systems and methods for processing biomass provides only some examples of operating environments within which functions and methods described herein may be implemented. Other operating environments and configurations of extraction vessels, distillery systems, speedloader/discharge gantry components and related components not explicitly described herein may also be applicable and suitable for implementation of the systems and methods.

The description above discloses, among other things, various example systems, methods, apparatus, and articles of manufacture. It is understood that such examples are merely illustrative and should not be considered as limiting. Accordingly, the examples provided are not the only ways) to implement such systems, methods, apparatus, and/or articles of manufacture.

Additionally, references herein to "embodiment" means that a particular feature, structure, or characteristic described in connection with the embodiment can be included in at least one example embodiment of an invention. The appearances of this phrase in various places in the specification are not necessarily all referring to the same embodiment, nor are separate or alternative embodiments mutually exclusive of other embodiments. As such, the embodiments described herein, explicitly and implicitly understood by one skilled in the art, can be combined with other embodiments.

The specification is presented largely in terms of illustrative environments, systems, procedures, steps, logic blocks, processing, and other symbolic representations that directly or indirectly resemble the operations performed by the disclosed systems. These process descriptions and representations are typically used by those skilled in the art to most effectively convey the substance of their work to others skilled in the art. Numerous specific details are set forth to provide a thorough understanding of the present disclosure. However, it is understood to those skilled in the art that certain embodiments of the present disclosure can be practiced without certain, specific details. In other instances, well known methods, procedures, components, and circuitry have not been described in detail to avoid unnecessarily obscuring aspects of the embodiments. Accordingly, the scope of the present disclosure is defined by the appended claims rather than the foregoing description of embodiments.

What is claimed is:

1. A method for yielding a reduced viscosity *cannabis* distillate, the method comprising:
    vacuum sealing an extraction vessel containing *cannabis* comprising cannabinoids;
    while the extraction vessel is vacuum sealed, washing the *cannabis* within the extraction vessel with a process solvent selected from the group consisting of (i) 1,1,2 Trans-dichloroethylene, (ii) 1,1,2 Trans-dichloroethylene R1234yf (2,3,3,3-Tetrafluoropropene), (iii) R134a (1,1,1,2-Tetrafluoroethane), (iv) R-32 (Difluoromethane), (v) R-125 (Pentafluoroethane), (vi) R441A (blend of ethane, propane, butane and isobutane/Hexafluoroethane), (vii) 1336mzz-z (cis-1,1,1,4,4,4-hexafluorobut-2-ene); (viii) t-DCE (trans-dichloroethylene), (ix) a blend comprising 70 wt. % or more of trans-1, 2-dichloroethylene (t-DCE) 0.1 to about 30 wt. % of one or more of hydrofluoroether (HFE) and n-propyl bromide, and (x) a blend consisting essentially of 1,1,2,2-tetrafluoroethyl-2,2,2-trifluoroethyl ether (R347), trans-1,2-dichloroethylene (tDCE) and a C-alcohol (ROH), wherein an amount of (R347) is from 25.0 to 75.0% by mass, an amount of (tDCE) is from 15.0 to 74.9% by mass and an amount of (ROH) is from 0.1 to 10.0% by mass, to a total amount of (R347), (tDCE) and (ROH), wherein at least some of the process solvent is in vaporized form, and wherein washing the *cannabis* with the process solvent causes at least some of the cannabinoids within the *cannabis* to separate from the *cannabis* thereby resulting in a *cannabis* extract comprising cannabinoids and the process solvent and processed *cannabis*, wherein the processed *cannabis* comprises residual process solvent;
    after washing the *cannabis* with the process solvent, returning the extraction vessel to atmospheric pressure, thereby causing the *cannabis* extract to transition from a vapor *cannabis* extract to a liquid *cannabis* extract;
    distilling the liquid *cannabis* extract, thereby separating the process solvent within the liquid *cannabis* extract from the cannabinoids within the liquid *cannabis* extract, which will result in (i) a recovered process solvent and (ii) a liquid *cannabis* distillate containing cannabinoids;
    routing the recovered process solvent to a recovered process solvent holding tank to hold the liquid *cannabis* distillate containing cannabinoids;
    creating a reduced-viscosity distillate by adding a transport solvent to the liquid *cannabis* distillate containing cannabinoids; and
    routing the reduced-viscosity distillate to a distillate holding tank to yield a reduced viscosity liquid *cannabis* distillate.

2. The method of claim 1, wherein distilling the liquid *cannabis* extract comprises heating the liquid *cannabis* extract to a temperature that is at least one of (i) between about 100° F. and about 130° F. or (ii) a sufficient temperature to boil the process solvent.

3. The method of claim 1, wherein distilling the liquid *cannabis* extract comprises heating the liquid *cannabis* extract to a temperature that is at least one of (i) more than about 135° F. or (ii) a sufficient temperature to cause decarboxylation of the cannabinoids.

4. The method of claim 1, further comprising:
    after returning the extraction vessel to atmospheric pressure, cooling the liquid *cannabis* extract contained within the extraction vessel to a temperature sufficient to precipitate undesirable solids from the liquid *cannabis* extract; and
    after precipitating at least some of the undesirable solids from the liquid *cannabis* extract, filtering the undesirable solids from the liquid *cannabis* extract before distilling the liquid *cannabis* extract.

5. The method of claim 4, wherein cooling the liquid *cannabis* extract contained within the extraction vessel to a temperature sufficient to precipitate at least some of the undesirable solids from the liquid *cannabis* extract comprises cooling the liquid *cannabis* extract to a temperature between about −20° F. to about −60° F.

6. The method of claim 5, wherein cooling the liquid *cannabis* extract contained within the extraction vessel to a temperature sufficient to precipitate at least some of the undesirable solids from the liquid *cannabis* extract further comprises vacuum sealing the extraction vessel again and cooling the liquid *cannabis* extract while the extraction vessel is vacuum sealed.

7. The method of claim 1, further comprising:
    evaporating at least some residual process solvent within the processed *cannabis* to generate air containing evaporated residual process solvent by one or both of (i) lowering air pressure within the extraction vessel containing the processed *cannabis* and (ii) applying light to the processed *cannabis* within the extraction vessel;
    routing air containing the evaporated residual process solvent to a process solvent reclamation condenser configured to condense the residual process solvent from the air containing the evaporated residual process solvent, resulting in liquid residual process solvent; and
    after evaporating at least some residual process solvent from the processed *cannabis*, facilitating removal of the processed *cannabis* from the extraction vessel.

8. The method of claim 1, wherein the *cannabis* comprises one or more of (i) wet *cannabis* having water content greater than about 70%, (ii) dry *cannabis*, or (iii) frozen *cannabis*.

9. The method of claim 1, wherein the *cannabis* comprises one or more of (i) a whole *cannabis* plant or (ii) a processed *cannabis* plant.

10. The method of claim 1, wherein vacuum sealing the extraction vessel containing the *cannabis* comprises vacuum sealing the extraction vessel at a vacuum level of about 28 Hg.

11. The method of claim 1, wherein, while the extraction vessel is vacuum sealed, washing the *cannabis* within the extraction vessel with the process solvent comprises:
    washing the *cannabis* within the extraction vessel with the process solvent via two or more washing cycles.

12. The method of claim 1, wherein the transport solvent comprises ethanol, and wherein creating the reduced-viscosity distillate by adding the transport solvent to the distillate comprises:

adding ethanol to the distillate comprising the cannabinoids to generate a reduced-viscosity distillate comprising between about 5% to 10% ethanol.

\* \* \* \* \*